United States Patent
Gomez-Mancilla et al.

(10) Patent No.: US 8,703,809 B2
(45) Date of Patent: Apr. 22, 2014

(54) COMBINATION PRODUCTS

(75) Inventors: Baltazar Gomez-Mancilla, Basel (CH); Fabrizio Gasparini, Lausen (CH)

(73) Assignee: Novartis AG, Basel (CH)

( * ) Notice: Subject to any disclaimer, the term of this patent is extended or adjusted under 35 U.S.C. 154(b) by 343 days.

(21) Appl. No.: 12/999,634

(22) PCT Filed: Jun. 30, 2009

(86) PCT No.: PCT/EP2009/058230
§ 371 (c)(1),
(2), (4) Date: Dec. 17, 2010

(87) PCT Pub. No.: WO2010/000763
PCT Pub. Date: Jan. 7, 2010

(65) Prior Publication Data
US 2012/0122878 A1   May 17, 2012

Related U.S. Application Data

(60) Provisional application No. 61/076,772, filed on Jun. 30, 2008.

(51) Int. Cl.
| | |
|---|---|
| *A01N 43/38* | (2006.01) |
| *A61K 31/40* | (2006.01) |
| *A01N 37/44* | (2006.01) |
| *A01N 37/12* | (2006.01) |
| *A61K 31/195* | (2006.01) |
| *C07D 209/32* | (2006.01) |
| *C07D 209/46* | (2006.01) |
| *C07C 229/00* | (2006.01) |

(52) U.S. Cl.
USPC ............ 514/421; 514/561; 548/512; 562/442

(58) Field of Classification Search
USPC ................... 514/421, 561; 548/512; 562/442
See application file for complete search history.

(56) References Cited

U.S. PATENT DOCUMENTS

| 7,683,063 B2 | 3/2010 | Kyle et al. | |
|---|---|---|---|
| 2003/0109504 A1* | 6/2003 | Brotchie et al. | 514/150 |
| 2005/0065191 A1* | 3/2005 | Gasparini et al. | 514/357 |

FOREIGN PATENT DOCUMENTS

| WO | WO 2004/024074 | 3/2004 |
|---|---|---|
| WO | WO 2004/089308 | 10/2004 |
| WO | WO 2005/030128 | 4/2005 |
| WO | WO 2007/071358 | 6/2007 |
| WO | WO 2007/143422 | 12/2007 |
| WO | WO 2008/015269 | 2/2008 |
| WO | WO 2008/031550 | 3/2008 |
| WO | WO 2009/047296 | 4/2009 |

OTHER PUBLICATIONS

Gennaro et. al. as editors, Remington: The Science and Practice of Pharmacy, 2005, Lippincott Williams & Wilkins, part 8B, p. 2033.*
Dekundy, A., et al., "Effects of group I metabotropic glutamate receptors blockage in experimental models of Parkinson's disease," Brain Res. Bull. Apr. 14, 2006;69(3):318-26.
Shtok, V.N., et al., "Treatment of Parkinson's Disease","Psychiatry and psychopharmacotherapy", 2000;2 No. 3.

* cited by examiner

*Primary Examiner* — Sarah Pihonak
(74) *Attorney, Agent, or Firm* — Jim Lynch

(57) ABSTRACT

The invention concerns the combinations of an mGluR modulator, e.g. an mGluR5 modulator and at least one of L-dopa, a dopamine modulator, e.g. a dopamine agonist, a dopa decarboxylase inhibitor or a catechol-O-methyl transferase inhibitor.

2 Claims, No Drawings

COMBINATION PRODUCTS

This application is a 371 of PCT/EP2009/058230 filed on Jun. 30, 2009, which claims benefit of U.S. Provisional Application No. 61/076,772 filed on Jun. 30, 2008, which in their entirety are herein incorporated by reference.

Dopamine agonists are, for example, bromocriptine, pergolide, pramipexole, ropinirole, cabergoline, apomorphine or lisuride.

Preferably the combination is a pharmaceutical composition or a combined pharmaceutical preparation.

In this pharmaceutical composition, the combination partners i.e. a metabotropic glutamate receptor modulator or a pharmaceutically acceptable slat thereof, and at least one of
 i) L-dopa, or
 ii) a dopa decarboxylase inhibitor, or
 iii) a catechol-O-methyl transferase inhibitor
 iv) a dopamine agonist
can be administered together, one after the other or separately in one combined unit dosage form or in two separate unit dosage forms. The unit dosage form may also be a fixed combination.

As used herein, the term "combinations" shall be taken to mean one or more substances which can be administered together, one after the other or separately in one combined unit dosage form or in two separate unit dosage forms.

Administration of the dosage forms may be co-cominantly, simultaneously, part-simultaneously, separately or sequentially. The dosage forms of the combination may not necessarily be of the same dosage form and may comprise one or more of:
Enteral: Oral (capsule, tablet, solution), Rectal (suppository)
Parenteral: Intravenous injection, subcutaneous injection, intramuscular injection, intraperitoneal injection, intramammary injection
Respiratory: Inhalation, Intranasal, Intratracheal
Topical: Mucous membrane application, skin application.

In addition, the release profiles of the mediciaments may not be the same, for example one or more component of the combination may be of extended release form.

It has recently been found that compounds having mGluR modulating activity, in particular antagonistic activity, may be used to treat Parkinson's Disease and disorders associated with Parkinson's Disease.

In particular, it has been found that mGluR modulators may be used to treat dyskensia, a disorder associated with Parkinson's Disease and treatment thereof. In particular, it has been found that mGluR5 modulators, e.g. mGluR5 antagonists, may be used to treat Parkinson's Disease and associated disorders e.g. Parkinson's dyskensia, for example, Parkinson's Disease levodopa (L-dopa) induced Parkinson's dyskensia.

It has now been surprisingly found that a combination comprising modulators of metabotropic glutamate receptors e.g. as defined below and, at least one compound selected from the group consisting of L-dopa, a dopamine agonist, a dopa decarboxylase inhibitor or a catechol-O-methyl transferase inhibitor has a beneficial effect and is useful in the treatment of disorders or conditions/disorders that might be treated by metabotropic glutamate receptor modulation, such as Parkinson's Disease and/or disorders associated therewith, for example.

Accordingly, a first aspect of the invention concerns the use of an mGluR modulator in combination with a second active agent for the treatment (whether therapeutic or prophylactic), prevention and/or delay of progression of Parkinson's Disease and/or disorders associated therewith.

In one embodiment, the invention concerns the use of an mGluR modulator e.g. an antagonist, in combinations with a second agent for the treatment, prevention and/or delay of progression of Parkinson's dyskensia, for example, Parkinson's Disease levodopa (L-dopa) induced dyskensia (PD-LID).

In one embodiment of the invention a specific combination is used. Said combination comprises:
an agent of the invention, especially an mGluR5 modulator; and
L-dopa;
at least one active agent selected from the group consisting of carbidopa, benserazide tolcapone, entacapone, bromocriptine, pergolide, pramipexole, ropinirole, cabergoline, apomorphine or lisuride.

In another embodiment of the invention a specific combination is used. Said combination comprises:
an agent of the invention, especially an mGluR5 modulator; and
at least one active agent selected from the group consisting of L-dopa, carbidopa, benserazide tolcapone, entacapone, bromocriptine, pergolide, pramipexole, ropinirole, cabergoline, apomorphine or lisuride.

A further aspect of the invention relates to a method for the treatment, prevention or delay of progression of Parkinson's Disease and/or disorders associated with Parkinson's disease in a subject in need of such treatment, which comprises administering to said subject a therapeutically effective amount of an mGluR, e.g. mGluR5, modulator in combination with a second agent, e.g. at least one compound selected from the group consisting of L-dopa, a dopamine agonist, a dopa decarboxylase inhibitor, or a catechol-O-methyl transferase inhibitor.

In one embodiment, the method is for the treatment, prevention and/or delay of progression of Parkinson's dyskensia, for example, Parkinson's Disease levodopa (L-dopa) induced dyskensia (PD-LID).

A further aspect of the invention relates to a pharmaceutical composition comprising an mGluR, e.g. mGluR5, modulator for the treatment, prevention or delay of progression of Parkinson's Disease and/or disorders associated with Parkinson's disease in combination with a second agent, e.g. at least one compound selected from the group consisting of L-dopa, a dopa decarboxylase inhibitor, or a catechol-O-methyl transferase inhibitor. In one embodiment, the composition is for the treatment, prevention or delay of progression of Parkinson's dyskensia e.g. Parkinson's Disease levodopa (L-dopa) induced dyskensia (PD-LID). In one embodiment, the pharmaceutical composition is for the treatment, prevention or delay of progression of Parkinson's Disease.

A further aspect of the invention relates to the use of an mGluR, e.g. mGluR5, modulator in combination with a second agent, e.g. at least one compound selected from the group consisting of L-dopa, a dopa decarboxylase inhibitor, or a catechol-O-methyl transferase inhibitor for the manufacture of a medicament for the treatment, prevention or delay of progression of Parkinson's Disease and/or disorders associated with Parkinson's disease. In one embodiment, the medicament is for the treatment, prevention or delay of progression of Parkinson's dyskensia e.g. Parkinson's Disease levodopa (L-dopa) induced dyskensia (PD-LID).

The mGluR modulator may be an mGluR5 modulator. In certain embodiments, the mGluR modulator is an mGluR, e.g. mGluR5, antagonist.

A disorder of particular interest is Parkinson's dyskinesia induced by L-dopa.

The agents of the invention, especially modulators of mGluR5 receptors, are useful in the treatment, prevention or delay of progression of Parkinson's dyskinesia e.g. Parkinson's Disease L-dopa induced dyskinesia. Parkinson's dyskinesia often, although not exclusively, occurs as a side-effect of treatment of Parkinson's disease with levodopa (L-dopa), a precursor of dopamine. Characteristics of Parkinson's dyskinesia include motor impairment, e.g. the appearance of slow and uncoordinated involuntary movements, shaking, stiffness and problems walking. Patients treated with L-dopa often have reduced symptoms of Parkinson's disease but they experience increasing difficulties to remain standing or even sitting. After prolonged use of L-dopa, a majority of patients develop dyskinesia.

Dyskinesia can occur at any time during the cycle of treatment with L-dopa. In one embodiment, the mGluR modulators as described herein, in combination as described herein or alone are for the treatment of dyskinesia which occurs at the time of peak L-dopa plasma concentrations in the patient. In one embodiment, the mGluR modulators as described herein, in combination as described herein or alone are for the treatment of dyskinesia which occurs when the L-dopa plasma concentrations in a patient rise or fall (diphasic dyskinesia).

Dyskinesia can also develop in Parkinson's disease sufferers who do not take L-dopa. In one embodiment, the compounds are for the treatment of non-L-dope induced Parkinson's dyskinesia.

Treatment with an agent of the invention in combination with a second agent, e.g. at least one compound selected from the group consisting of L-dopa, a dopa decarboxylase inhibitor, or a catechol-O-methyl transferase inhibitor may comprise a reduction in the characteristics associated with Parkinson's dyskinesia, including for example, although not limited to, a reduction in the scale of involuntary movements, a reduction in the number of involuntary movements, an improvement in the ability to carry out normal tasks, an improved ability to walk, increased period of time between episodes of dyskinesia.

In the case of prophylactic treatment, the agents of the invention, especially the agents as defined in list P, may be used to delay or prevent the onset of Parkinson's dyskinesia.

In the present specification, the following definitions shall apply if no specific other definition is given:

"Alkyl" represents a straight-chain or branched-chain alkyl group, preferably represents a straight-chain or branched-chain $C_{1-12}$ alkyl, particularly preferably represents a straight-chain or branched-chain $C_{1-6}$ alkyl; for example, methyl, ethyl, n- or iso-propyl, n-, iso-, sec- or tert-butyl, n-pentyl, n-hexyl, n-heptyl, n-octyl, n-nonyl, n-decyl, n-undecyl, n-dodecyl, with particular preference given to methyl, ethyl, n-propyl and iso-propyl.

"Alkandiyl" represents a straight-chain or branched-chain alkandiyl group bound by two different carbon atoms to the molecule, it preferably represents a straight-chain or branched-chain $C_{1-12}$ alkandiyl, particularly preferably represents a straight-chain or branched-chain $C_{1-6}$ alkandiyl; for example, methandiyl (—$CH_2$—), 1,2-ethanediyl(—$CH_2$—$CH_2$—), 1,1-ethanediyl((—$CH(CH_3)$—), 1,1-, 1,2-, 1,3-propanediyl and 1,1-, 1,2-, 1,3-, 1,4-butanediyl, with particular preference given to methandiyl, 1,1-ethanediyl, 1,2-ethanediyl, 1,3-propanediyl or 1,4-butanediyl.

Each alkyl part of "alkoxy", "alkoxyalkyl", "alkoxycarbonyl", "alkoxycarbonylalkyl" and "halogenalkyl" shall have the same meaning as described in the above-mentioned definition of "alkyl".

"Alkenyl" represents a straight-chain or branched-chain alkenyl group, preferably $C_{2-6}$ alkenyl, for example, vinyl, allyl, 1-propenyl, isopropenyl, 2-butenyl, 2-pentenyl, 2-hexenyl, etc. and preferably represents $C_{2-4}$ alkenyl.

"Alkendiyl" represents a straight-chain or branched-chain alkendiyl group bound by two different carbon atoms to the molecule, it preferably represents a straight-chain or branched-chain $C_{2-6}$ alkandiyl; for example, —CH=CH—, —CH=C(CH$_3$)—, —CH=CH—CH$_2$—, —C(CH$_3$)=CH—CH$_2$—, —CH=C(CH$_3$)—CH$_2$—, —CH=CH—C(CH$_3$)H—, —CH=CH—CH=CH—, —C(CH$_3$)=CH—CH=CH—, —CH=C(CH$_3$)—CH=CH—, with particular preference given to —CH=CH—CH$_2$—, —CH=CH—CH=CH—.

"Alkynyl" represents a straight-chain or branched-chain alkynyl group, preferably $C_{2-6}$ alkynyl, for example, ethenyl, propargyl, 1-propynyl, isopropenyl, 1-(2- or 3) butynyl, 1-(2- or 3) pentenyl, 1-(2- or 3) hexenyl, etc., preferably represents $C_{2-4}$ alkynyl and particularly preferably represents ethynyl.

"Aryl" represents an aromatic hydrocarbon group, preferably a $C_{6-10}$ aromatic hydrocarbon group; for example phenyl, naphthyl, especially phenyl.

"Aralkyl" denotes an "aryl" bound to an "alkyl" (both as defined above) an represents, for example benzyl, α-methylbenzyl, 2-phenylethyl, α,α-dimethylbenzyl, especially benzyl.

"Heterocycle" represents a saturated, partly saturated or aromatic ring system containing at least one hetero atom. Preferably, heterocycles consist of 3 to 11 ring atoms of which 1-3 ring atoms are hetero atoms. Heterocycles may be present as a single ring system or as bicyclic or tricyclic ring systems; preferably as single ring system or as benz-annelated ring system. Bicyclic or tricyclic ring systems may be formed by annelation of two or more rings, by a bridging atom, e.g. oxygen, sulfur, nitrogen or by a bridging group, e.g. alkandiyl or alkenediyl. A heterocycle may be substituted by one or more substituents selected from the group consisting of oxo (=O), halogen, nitro, cyano, alkyl, alkandiyl, alkenediyl, alkoxy, alkoxyalkyl, alkoxycarbonyl, alkoxycarbonylalkyl, halogenalkyl, aryl, aryloxy and arylalkyl. Examples of heterocyclic moieties include pyrrole, pyrroline, pyrrolidine, pyrazole, pyrazoline, pyrazolidine, imidazole, imidazoline, imidazolidine, triazole, triazoline, triazolidine, tetrazole, furane, dihydrofurane, tetrahydrofurane, furazane (oxadiazole), dioxolane, thiophene, dihydrothiophene, tetrahydrothiophene, oxazole, oxazoline, oxazolidine, isoxazole, isoxazoline, isoxazolidine, thiazole, thiazoline, thiaziolidine, isothiazole, istothiazoline, isothiazolidine, thiadiazole, thiadiazoline, thiadiazolidine, pyridine, piperidine, pyridazine, pyrazine, piperazine, triazine, pyrane, tetrahydropyrane, thiopyrane, tetrahydrothiopyrane, oxazine, thiazine, dioxine, morpholine, purine, pterine, and the corresponding benz-annelated heterocycles, e.g. indole, isoindole, cumarine, cumaronecinoline, isochinoline, cinnoline and the like.

"Hetero atoms" are atoms other than carbon and hydrogen, preferably nitrogen (N), oxygen (O) or sulfur (S).

"Halogen" represents fluoro, chloro, bromo or iodo, preferably represents fluoro, chloro or bromo and particularly preferably represents chloro.

Various compounds having mGluR, in particular mGluR5, modulating activity are described herein. Where the specification refers to compounds, agents or active ingredients of the invention, this is generally taken to mean a compound having mGluR modulating activity unless specified otherwise. In embodiments of the invention, the mGluR modulators are mGluR5 antagonists. When the specification refers to mGluR antagonists, this is generally taken to include compounds that are capable of interacting with an mGluR to inhibit the effect of a natural ligand for the mGluR e.g. such that a response pathway of a mGluR expressing cell is not stimulated.

In one embodiment, the mGluR modulator is a mGluR5 antagonist.

The mGluR modulators as described herein may exist in free or acid addition salt form. In this specification, unless otherwise indicated, reference to "the mGluR modulators as described herein" is to be understood as embracing the compounds in any form, for example free base or acid addition salt form. Salts which are unsuitable for pharmaceutical uses but which can be employed, for example, for the isolation or purification of free the mGluR modulators as described herein, such as picrates or perchlorates, are also included. For therapeutic use, only pharmaceutically acceptable salts or free compounds are employed (where applicable in the form of pharmaceutical preparations), and are therefore preferred.

It will be understood that any discussion of methods or references to the active ingredients also includes pharmaceutically acceptable salts. If these active ingredients have, for example, at least one basic center, they can form acid addition salts. Corresponding acid addition salts can also be formed having, if desired, an additionally present basic center. The active ingredients having an acid group (for example COOH) can also form salts with bases. The active ingredient or a pharmaceutically acceptable salt thereof may also be used in the form of a hydrate or may include other solvents used for crystallization. Examples of mGluR5 modulators, e.g. antagonists, and their manufacture are known, e.g. from WO 03/047581 and WO 2006/114262, both of which are incorporated herein by reference.

On account of the asymmetrical carbon atom(s) that may be present in the mGluR modulators as described herein and their salts, the compounds may exist in optically active form or in form of mixtures of optical isomers, e.g. in form of racemic mixtures or diastereomeric mixtures. All optical isomers and their mixtures, including racemic mixtures, are part of the present invention.

In one embodiment, the mGluR modulator is a compound of the formula (I)

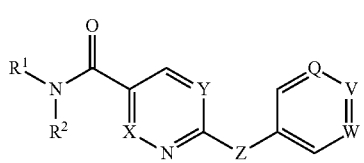

(I)

wherein
$R^1$ represents optionally substituted alkyl or optionally substituted benzyl; and
$R^2$ represents hydrogen (H), optionally substituted alkyl or optionally substituted benzyl; or
$R^1$ and $R^2$ form together with the nitrogen atom to which they are attached an optionally substituted heterocycle with less than 14 ring atoms;
$R^3$ represents halogen, alkyl, alkoxy, alkylamino or dialkylamino;
$R^4$ represents hydroxy (OH), halogen, alkyl or alkoxy;
Q represents CH, $CR^4$ or N;
V represents CH, $CR^4$ or N;
W represents CH, $CR^4$ or N;
X represents CH or N;

Y represents CH, $CR^3$ or N;
Z represents $CH_2$, NH or O; and
provided that Q, V and W are not N at the same time;
in free base or acid addition salt form.

In another embodiment, the mGluR modulator is a compound of the formula (II), wherein a compound of the formula (II) is a compound of formula (I) in which at least one of Q, V and W is N; in free base or acid addition salt form.

In yet a further embodiment, the mGluR modulator is a compound of the formula (III), wherein a compound of the formula (III) is a compound of formula (II) in which Y is $CR^3$; in free base or acid addition salt form.

Preferred substituents, preferred ranges of numerical values or preferred ranges of the radicals present in the formula (I), (II) and (III) and the corresponding intermediate compounds are defined below.

X preferably represents CH.

Y preferably represents CH or $CR^3$, wherein $R^3$ preferably represents halogen, particular preferably chloro.

Z preferably represents NH.

$R^3$ preferably represents fluoro, chloro, $C_{1-4}$ alkyl, e.g. methyl.

$R^3$ particularly preferably represents chloro.

$R^1$ and $R^2$ preferably form together with the nitrogen atom to which they are attached an unsubstituted or substituted heterocycle having 3-11 ring atoms and 1-4 hetero atoms; the hetero atoms being selected from the group consisting of N, O, S, the substituents being selected from the group consisting of oxo (=O), hydroxy, halogen, amino, nitro, cyano, $C_{1-4}$ alkyl, $C_{1-4}$ alkoxy, $C_{1-4}$ alkoxyalkyl, $C_{1-4}$ alkoxycarbonyl, $C_{1-4}$ alkoxycarbonylalkyl, $C_{1-4}$ halogenalkyl, $C_{6-10}$ aryl, halogen-$C_{6-10}$ aryl, $C_{6-10}$ aryloxy and $C_{6-10}$-aryl-$C_{1-4}$ alkyl.

$R^1$ and $R^2$ form together with the nitrogen atom to which they are attached form an unsubstituted, a single or twofold substituted heterocycle having 5-9 ring atoms and 1-3 hetero atoms; the hetero atoms being selected from the group consisting of N and O; the substituents being selected from the group consisting of halogen and $C_{1-4}$ alkyl.

$R^1$ and $R^2$ preferably form together with the nitrogen atom to which they are attached an unsubstituted, a single or twofold substituted heterocycle selected from the group consisting of

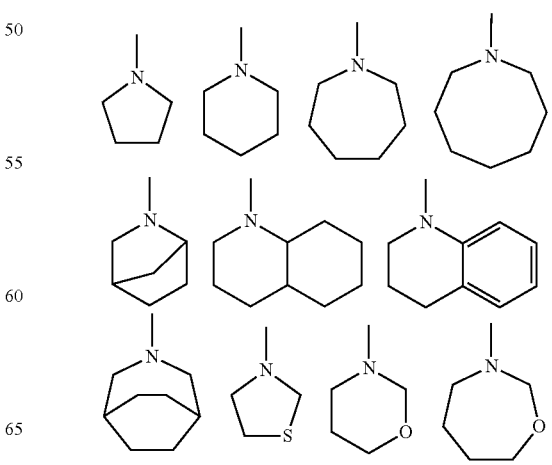

and the substituents being selected from the group consisting of fluoro, chloro, methyl, ethyl, propyl, butyl, trifluoromethyl, fluoropropyl and difluoropropyl.

$R^1$ and $R^2$ preferably represent, independently from each other, $C_1$-$C_4$ alkyl or benzyl, optionally substituted by $C_1$-$C_4$ alkoxy or halogen.

The above mentioned general or preferred radical definitions apply both to the end products of the formulae (I), (II) and (III) and also, correspondingly, to the starting materials or intermediates required in each case for the preparation. These radical definitions can be combined with one another at will, i.e. including combinations between the given preferred ranges. Further, individual definitions may not apply.

Preference according to the invention is given to compounds of the formulae (I), (II) and (III) which contain a combination of the meanings mentioned above as being preferred.

Particular preference according to the invention is given to compounds of the formulae (I), (II) and (III) which contain a combination of the meanings listed above as being particularly preferred.

Very particular preference according to the invention is given to the compounds of the formula (I) which contain a combination of the meanings listed above as being very particularly preferred.

Preferred are those compounds of formulae (I), (II) and (III) wherein $R^2$ represents an unsubstituted or substituted heterocycle.

Particular preferred are compounds of formulae (I), (II) to (III) as shown below:

(IIa)

wherein the substituents have the meaning given in this specification;

(IIb)

wherein the substituents have the meaning given in this specification;

(IIc)

wherein the substituents have the meaning given in this specification;

(IId)

wherein $R^4$ represents $C_1$-$C_4$ alkyl, preferably methyl, and the other substituents have the meaning given in this specification;

(IIe)

wherein $R^4$ represents halogen, preferably chloro, and the other substituents have the meaning given in this specification.

Further preferred compounds of the present invention have the formulae (IIIa to IIIe) as shown below:

(IIIa)

wherein all of the substituents have the meaning given in this specification;

(IIIb)

wherein the substituents have the meaning given in this specification;

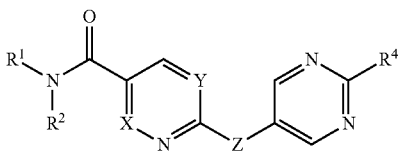

wherein the substituents have the meaning given in this specification;

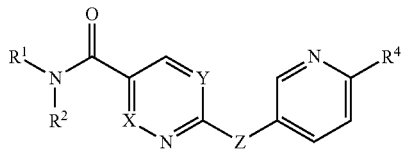

wherein R⁴ represents $C_1$-$C_4$ alkyl, preferably methyl, and the other substituents have the meaning given in this specification;

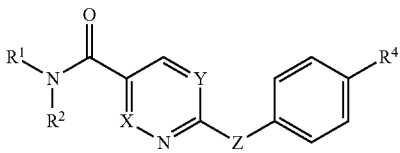

wherein R⁴ represents halogen, preferably chloro, and the other substituents have the meaning given in this specification.

Particular compounds of the formulae (I), (II) and (III) include those described in the Examples given herein.

In another embodiment, the mGluR modulator is a compound of the formula (IV):

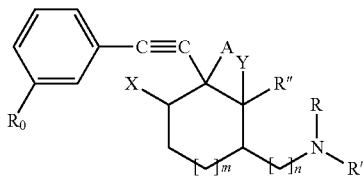

wherein
m is 0 or 1,
n is 0 or 1 and
A is hydroxy
X is hydrogen and
Y is hydrogen, or
A forms a single bond with X or with Y;
$R_0$ is hydrogen, $(C_{1-4})$alkyl, $(C_{1-4})$alkoxy, trifluoromethyl, halogen, cyano, nitro, —COOR₁
wherein $R_1$ is $(C_{1-4})$alkyl or —COR₂ wherein $R_2$ is hydrogen or $(C_{1-4})$alkyl, and
R is —COR₃, —COOR₃, —CONR₄R₅ or —SO₂R₆, wherein $R_3$ is $(C_{1-4})$alkyl, $(C_{3-7})$cycloalkyl or optionally substituted phenyl, 2-pyridyl or 2-thienyl; $R_4$ and $R_5$, independently, are hydrogen or $(C_{1-4})$alkyl; and $R_6$ is $(C_{1-4})$alkyl, $(C_{3-7})$ cycloalkyl or optionally substituted phenyl, R' is hydrogen or $(C_{1-4})$alkyl and
R" is hydrogen or $(C_{1-4})$alkyl, or
R' and R" together form a group —CH₂—(CH₂)ₘ—
wherein m is 0, 1 or 2, in which case one of n and m is different from 0,
with the proviso that $R_0$ is different from hydrogen, trifluoromethyl and methoxy when n is 0,
A is hydroxy, X and Y are both hydrogen, R is COOEt and R' and R" together form a group —(CH₂)₂—,
in free base or acid addition salt form.

Exemplary compounds of formula (IV) include:
(−)-(3aR,4S,7aR)-4-Hydroxy-4-m-tolylethynyl-octahydro-indole-1-carboxylic acid methyl ester
(−)-(3aR,4S,7aR)-4-Hydroxy-4-m-tolylethynyl-octahydro-indole-1-carboxylic acid ethyl ester
(−)-(3aR,4S,7aR)-Furan-2-yl-(4-hydroxy-4-m-tolylethynyl-octahydro-indol-1-yl)-methanone
(±)-(3aRS,4SR,7aRS)-4-(3-Chlorophenylethynyl)-4-hydroxy-octahydro-indole-1-carboxylic acid ethyl ester
(±)-(3aRS,4SR,7aRS)-4-(3-Fluoro-phenylethynyl)-4-hydroxy-octahydro-indole-1-carboxylic acid ethyl ester
(3aRS,4SR,7aRS)-4-Hydroxy-4-phenylethynyl-octahydro-indole-1-carboxylic acid(S)(tetrahydrofuran-3-yl)ester
(3aRS,4SR,7aRS)-4-Hydroxy-4-phenylethynyl-octahydro-indole-1-carboxylic acid (R)(tetrahydrofuran-3-yl)ester
(3aRS,4SR,7aRS)-4-Hydroxy-4-(3-chlorophenylethynyl)-octahydro-indol-1-carboxylic acid-(S)(tetrahydrofuran-3yl)ester
(±)-(3aRS,4SR,7aRS)-4-Hydroxy-4-m-tolylethynyl-octahydro-indole-1-carboxylic acid ethyl ester
(±)-(3aRS,4SR,7aRS)-4-(4-Fluoro-phenylethynyl)-4-hydroxy-octahydro-indole-1-carboxylic acid ethyl ester
(±)-(3aRS,4SR,7aRS)-4-(3-chlorophenylethynyl)-4-hydroxy-1-methanesulfonyl-octahydro-indole
(±)-(3aRS,7aRS)-4-Phenylethynyl-2,3,3a,6,7,7a-hexahydro-indole-1-carboxylic acid ethyl ester and (±)-(RS)-4-phenylethynyl-2,3,5,6,7,7a-hexahydro-indole-1-carboxylic acid ethyl ester
(±)-(3RS,7aRS)-2,2,2-Trifluoro-1-(4-phenylethynyl-2,3,3a, 6,7,7a-hexahydro-indol-1-yl)-ethanone
(±)-(RS)-4-m-Tolylethynyl-2,3,5,6,7,7a-hexahydro-indole-1-carboxylic acid ethyl ester
(±)-(3RS,7aRS)-4-m-Tolylethynyl-2,3,3a,6,7,7a-hexahydro-indole-1-carboxylic acid ethyl ester
(±)-(3RS,7aRS)-4-(4-Chloro-phenylethynyl)-2,3,3a,6,7,7a-hexahydro-indole-1-carboxylic acid ethyl ester
(±)-(3RS,7aRS)-4-(2-Fluoro-phenylethynyl)-2,3,3a,6,7,7a-hexahydro-indole-1-carboxylic acid ethyl ester
(±)-(3RS,7aRS)-4-(3-Fluoro-phenylethynyl)-2,3,3a,6,7,7a-hexahydro-indole-1-carboxylic acid ethyl ester
(±)-(RS)-4-(3-Fluoro-phenylethynyl)-2,3,5,6,7,7a-hexahydro-indole-1-carboxylic acid ethyl ester
(±)-(3RS,7aRS)-4-(3-Methoxy-phenylethynyl)-2,3,3a,6,7, 7a-hexahydro-indole-1-carboxylic acid ethyl ester
(±)-(RS)-4-(3-Methoxy-phenylethynyl)-2,3,5,6,7,7a-hexahydro-indole-1-carboxylic acid ethyl ester
(±)-(3aRS,4RS,7aSR)-4-Hydroxy-4-phenylethynyl-octahydro-isoindole-2-carboxylic acid ethyl ester
(±)-(3aRS,4RS,7aSR)-4-Hydroxy-4-m-tolylethynyl-octahydro-isoindole-2-carboxylic acid ethyl ester
(±)-(3aRS,4RS,7aSR)-4-Hydroxy-4-p-tolylethynyl-octahydro-isoindole-2-carboxylic acid ethyl ester
(±)-(3aRS,4RS,7aSR)-4-(3-Cyano-phenylethynyl)-4-hydroxy-octahydro-isoindole-2-carboxylic acid ethyl ester
(±)-(3aRS,4RS,7aSR)-4-Hydroxy-4-(3-methoxy-phenylethynyl)-octahydro-isoindole-2-carboxylic acid ethyl ester (±)-(3aRS,4RS,7aSR)-4-(3-Fluoro-phenylethynyl)-4-hydroxy-octahydro-isoindole-2-carboxylic acid ethyl ester
(±)-(3aRS,4RS,7aSR)-4-Hydroxy-4-phenylethynyl-octahydro-isoindole-2-carboxylic acid tert-butyl ester
(±)-(3aRS,4RS,7aSR)-4-Hydroxy-4-m-tolylethynyl-octahydro-isoindole-2-carboxylic acid tert-butyl ester
(±)-(3aRS,4RS,7aSR)-4-Hydroxy-4-m-tolylethynyl-octahydro-isoindole-2-carboxylic acid methyl ester
(±)-(3aRS,4RS,7aSR)-Furan-2-yl-(4-hydroxy-4-m-tolylethynyl-octahydro-isoindol-2-yl)-methanone
(±)-(3aRS,4RS,7aSR)-Cyclopropyl-(4-hydroxy-4-m-tolylethynyl-octahydro-isoindol-2-yl)-methanone
(±)-(3aRS,4RS,7aSR)-(4-Hydroxy-4-m-tolylethynyl-octahydro-isoindol-2-yl)-pyridin-3-yl-methanone
(±)-((1SR,3SR)-3-Hydroxy-3-m-tolylethynyl-cyclohexyl)-methyl-carbamic acid methyl ester and (±)-((1RS,3SR)-3-hydroxy-3-m-tolylethynyl-cyclohexyl)-methyl-carbamic acid methyl ester
(±)-(1RS,3SR)-((3-Hydroxy-3-m-tolylethynyl-cyclohexyl)-(4-methoxy-benzyl)-carbamic acid ethyl ester
(±)-(1RS,3RS)-((3-Hydroxy-3-m-tolylethynyl-cyclohexyl)-(4-methoxy-benzyl)-carbamic acid ethyl ester
(±)-[(1RS,3SR)-3-Hydroxy-3-(3-methoxy-phenylethynyl)-5,5-dimethyl-cyclohexyl]-methyl-carbamic acid methyl ester
(±)-(1RS,3SR)-(3-Hydroxy-5,5-dimethyl-3-m-tolylethynyl-cyclohexyl)-methyl-carbamic acid methyl ester
(±)-[(1RS,3SR)-3-(3-Fluoro-phenylethynyl)-3-hydroxy-5,5-dimethyl-cyclohexyl]-methyl-carbamic acid methyl ester
(±)-[(1RS,3RS)-3-(3-Fluoro-phenylethynyl)-3-hydroxy-cyclohexyl]-methyl-carbamic acid methyl ester
(±)-[(1RS,3SR)-3-(3-Fluoro-phenylethynyl)-3-hydroxy-cyclohexyl]-methyl-carbamic acid methyl ester
(±)-[(1RS,3RS)-3-Hydroxy-3-(3-methoxy-phenylethynyl)-cyclohexyl]-methyl-carbamic acid methyl ester
(±)-[(1RS,3SR)-3-Hydroxy-3-(3-methoxy-phenylethynyl)-cyclohexyl]-methyl-carbamic acid methyl ester
(±)-[(1RS,3RS)-3-(3-Chloro-phenylethynyl)-3-hydroxy-cyclohexyl]-methyl-carbamic acid methyl ester
(±)-[(1RS,3SR)-3-(3-Chloro-phenylethynyl)-3-hydroxy-cyclohexyl]-methyl-carbamic acid methyl ester
(±)-(1RS,3RS)—N-(3-hydroxy-3-m-tolylethynyl-cyclohexyl)-acetamide
(±)-(1RS,3SR)—N-(3-hydroxy-3-m-tolylethynyl-cyclohexyl)-acetamide
(±)-(1RS,3RS)-(3-Hydroxy-3-m-tolylethynyl-cyclohexyl)-carbamic acid ethyl ester
(±)-(1RS,3SR)-(3-Hydroxy-3-m-tolylethynyl-cyclohexyl)-carbamic acid ethyl ester
(±)-(1RS,3RS)-[3-(3-Fluoro-phenylethynyl)-3-hydroxy-cyclohexyl]-carbamic acid ethyl ester
(±)-(1RS,3SR)-[3-(3-Fluoro-phenylethynyl)-3-hydroxy-cyclohexyl]-carbamic acid ethyl ester
(±)-(1RS,3RS)-[3-(3-Methoxy-phenylethynyl)-3-hydroxy-cyclohexyl]-carbamic acid ethyl ester
(±)-(1RS,3RS)—N-[3-(3-Fluoro-phenylethynyl)-3-hydroxy-cyclohexyl]-acetamide.
(±)-(1RS,3SR)—N-[3-(3-Fluoro-phenylethynyl)-3-hydroxy-cyclohexyl]-acetamide
(±)-(1RS,3SR)-[3-Hydroxy-3-(3-methoxy-phenylethynyl)-cyclohexyl]-carbamic acid ethyl ester
(±)-(1RS,3RS)—N-[3-Hydroxy-3-(3-methoxy-phenylethynyl)-cyclohexyl]-acetamide
(±)-(1RS,3SR)—N-[3-Hydroxy-3-(3-methoxy-phenylethynyl)-cyclohexyl]-acetamide.
(±)-(1RS,3RS)-[3-Hydroxy-3-(3-methoxy-phenylethynyl)-cyclohexyl]-carbamic acid tert-butyl ester
(±)-(1RS,3SR)-[3-Hydroxy-3-(3-methoxy-phenylethynyl)-cyclohexyl]-carbamic acid tert-butyl ester
(±)-(1RS,3RS)-(3-Hydroxy-3-m-tolylethynyl-cyclohexyl)-carbamic acid tert-butyl ester
(±)-(1RS,3SR)-(3-Hydroxy-3-m-tolylethynyl-cyclohexyl)-carbamic acid tert-butyl ester
(±)-(1RS,3RS)-(3-(3-Fluoro-phenylethynyl)-3-hydroxy-cyclohexyl)-carbamic acid tert-butyl ester
(±)-(1RS,3SR)-(3-(3-Fluoro-phenylethynyl)-3-hydroxy-cyclohexyl)-carbamic acid tert-butyl ester
(±)-(1RS,3RS)-[3-(3-Fluoro-phenylethynyl)-3-hydroxy-cyclohexyl]-carbamic acid methyl ester
(±)-(1RS,3SR)-[3-(3-Fluoro-phenylethynyl)-3-hydroxy-cyclohexyl]-carbamic acid methyl ester
(±)-(3-Phenylethynyl-cyclohex-2-enyl)-carbamic acid ethyl ester and (±)-3-phenylethynyl-cyclohex-3-enyl)-carbamic acid ethyl ester
(±)-Methyl-(3-phenylethynyl-cyclohex-3-enyl)-carbamic acid ethyl ester
(±)-(4aRS,5RS,8aSR)-5-Hydroxy-5-phenylethynyl-octahydro-quinoline-1-carboxylic acid ethyl ester
(±)-[(4aRS,5SR,8aSR)-5-(3-Chloro-phenylethynyl)-5-hydroxy-octahydro-quinolin-1-yl]-furan-2-yl-methanone
(±)-[(4aRS,5RS,8aSR)-5-(3-Chloro-phenylethynyl)-5-hydroxy-octahydro-quinolin-1-yl]-furan-2-yl-methanone
(±)-(4aRS,5RS,8aSR)-5-(3-Chloro-phenylethynyl)-5-hydroxy-octahydro-quinoline-1-carboxylic acid tert-butyl ester
(±)-[(4aRS,5SR,8aSR)-5-(3-Chloro-phenylethynyl)-5-hydroxy-octahydro-quinolin-1-yl]-morpholin-4-yl-methanone
(±)-[(4aRS,5SR,8aSR)-5-(3-chloro-phenylethynyl)-5-hydroxy-octahydro-quinolin-1-yl]-(4-methyl-piperazin-1-yl)-methanone
(±)-(4aRS,5SR,8aSR)-5-(3-chloro-phenylethynyl)-5-hydroxy-octahydro-quinoline-1-carboxylic acid ethyl ester and (±)-(4aRS,5SR,8aSR)-5-(3-chloro-phenylethynyl)-5-hydroxy-octahydro-quinoline-1-carboxylic acid ethyl ester
(±)-(4aRS,5SR,8aSR)-5-Hydroxy-5-m-tolylethynyl-octahydro-quinoline-1-carboxylic acid ethyl ester
(±)-(4aRS,5RS,8aSR)-5-Hydroxy-5-m-tolylethynyl-octahydro-quinoline-1-carboxylic acid ethyl ester.

Compounds of formula (IV) are in particular an Octahydroindole.

In a particular example o the present invention, there is provided a combination of the above listed exemplary compounds of formula (IV) with at least one active agent selected from the group consisting of L-dopa, carbidopa, benserazide tolcapone or entacapone.

In a further embodiment, the mGluR modulator is a compound of the formula (V):

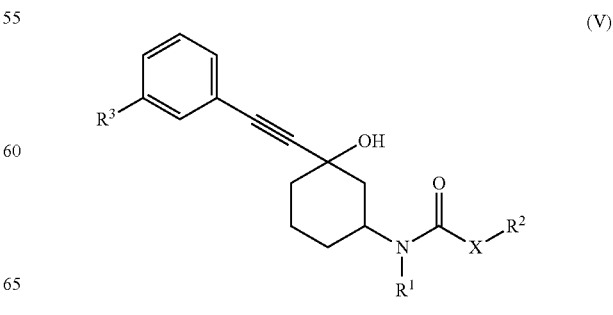

(V)

wherein
R¹ represents hydrogen or alkyl;
R² represents an unsubstituted or substituted heterocycle or
R² represents an unsubstituted or substituted aryl;
R³ represents alkyl or halogen;
X represents a single bond or an alkandiyl-group, optionally interrupted by one or more oxygen atoms or carbonyl groups or carbonyloxy groups
in free base or acid addition salt form.

Exemplary compounds of formula (V) include:
Furan-3-carboxylic acid [(1S,3S)-3-(3-chloro-phenylethynyl)-3-hydroxy-cyclohexyl]-amide
Furan-2-carboxylic acid [(1R,3R)-3-(3-chloro-phenylethynyl)-3-hydroxy-cyclohexyl]-amide
Furan-2-carboxylic acid [(1S,3S)-3-(3-chloro-phenylethynyl)-3-hydroxy-cyclohexyl]-amide
3H-Imidazole-4-carboxylic acid [(1R,3R)-3-(3-chloro-phenylethynyl)-3-hydroxy-cyclohexyl]-amide
3H-Imidazole-4-carboxylic acid [(1S,3S)-3-(3-chloro-phenylethynyl)-3-hydroxy-cyclohexyl]-amide
4H-[1,2,4]Triazole-3-carboxylic acid [(1R,3R)-3-(3-chloro-phenylethynyl)-3-hydroxy-cyclohexyl]-amide
4H-[1,2,4]Triazole-3-carboxylic acid [(1S,3S)-3-(3-chloro-phenylethynyl)-3-hydroxy-cyclohexyl]-amide
2-Methyl-furan-3-carboxylic acid [(±)-(1R,3R)-3-(3-chloro-phenylethynyl)-3-hydroxy-cyclohexyl]-amide
N-[(±)-(1R,3R)-3-(3-Chloro-phenylethynyl)-3-hydroxy-cyclohexyl]-3,4-difluoro-benzamide
Benzo[1,3]dioxole-2-carboxylic acid [(±)-(1R,3R)-3-(3-chloro-phenylethynyl)-3-hydroxy-cyclohexyl]-amide
5-Methyl-pyrazine-2-carboxylic acid [(±)-(1R,3R)-3-(3-chloro-phenylethynyl)-3-hydroxy-cyclohexyl]-amide
Quinoxaline-2-carboxylic acid [(±)-(1R,3R)-3-(3-chloro-phenylethynyl)-3-hydroxy-cyclohexyl]-amide
Benzofuran-2-carboxylic acid [(±)-(1R,3R)-3-(3-chloro-phenylethynyl)-3-hydroxy-cyclohexyl]-amide
Benzooxazole-2-carboxylic acid [(±)-(1R,3R)-3-(3-chloro-phenylethynyl)-3-hydroxy-cyclohexyl]-amide
2,5-Dimethyl-furan-3-carboxylic acid [(±)-(1R,3R)-3-(3-chloro-phenylethynyl)-3-hydroxy-cyclohexyl]-amide
(R,S)-Tetrahydro-furan-3-carboxylic acid [(±)-(1R,3R)-3-(3-chloro-phenylethynyl)-3-hydroxy-cyclohexyl]-amide
Furan-3-carboxylic acid ((1R,3R)-3-hydroxy-3-m-tolylethynyl-cyclohexyl)-amide
Furan-3-carboxylic acid ((1S,3S)-3-hydroxy-3-m-tolylethynyl-cyclohexyl)-amide
Furan-3-carboxylic acid ((±)-(1R,3R)-3-hydroxy-3-m-tolylethynyl-cyclohexyl)-amide
Furan-2-carboxylic acid ((1R,3R)-3-hydroxy-3-m-tolylethynyl-cyclohexyl)-amide
Furan-2-carboxylic acid ((1S,3S)-3-hydroxy-3-m-tolylethynyl-cyclohexyl)-amide
Furan-2-carboxylic acid ((±)-(1R,3R)-3-hydroxy-3-m-tolylethynyl-cyclohexyl)-amide
Isoxazole-5-carboxylic acid ((1R,3R)-3-hydroxy-3-m-tolylethynyl-cyclohexyl)-amide
Isoxazole-5-carboxylic acid ((1S,3S)-3-hydroxy-3-m-tolylethynyl-cyclohexyl)-amide
Isoxazole-5-carboxylic acid ((±)-(1R,3R)-3-hydroxy-3-m-tolylethynyl-cyclohexyl)-amide
5-Methyl-pyrazine-2-carboxylic acid ((±)-(1R,3R)-3-hydroxy-3-m-tolylethynyl-cyclohexyl)-amide
4H-[1,2,4]Triazole-3-carboxylic acid ((±)-(1R,3R)-3-hydroxy-3-m-tolylethynyl-cyclohexyl)-amide
3H-Imidazole-4-carboxylic acid ((±)-(1R,3R)-3-hydroxy-3-m-tolylethynyl-cyclohexyl)-amide
Tetrahydro-pyran-4-carboxylic acid ((±)-(1R,3R)-3-hydroxy-3-m-tolylethynyl-cyclohexyl)-amide
1-Methyl-1H-imidazole-4-carboxylic acid ((±)-(1R,3R)-3-hydroxy-3-m-tolylethynyl-cyclohexyl)-amide
(R,S)-Tetrahydro-furan-2-carboxylic acid ((±)-(1R,3R)-3-hydroxy-3-m-tolylethynyl-cyclohexylyamide
(R,S)-Tetrahydro-furan-3-carboxylic acid ((±)-(1R,3R)-3-hydroxy-3-m-tolylethynyl-cyclohexyl)-amide
Furan-3-carboxylic acid [(1R,3R)-3-(3-fluoro-phenylethynyl)-3-hydroxy-cyclohexyl]-amide
Furan-3-carboxylic acid [(1S,3S)-3-(3-fluoro-phenylethynyl)-3-hydroxy-cyclohexyl]-amide
Furan-2-carboxylic acid [(1R,3R)-3-(3-fluoro-phenylethynyl)-3-hydroxy-cyclohexyl]-amide
Furan-2-carboxylic acid [(1S,3S)-3-(3-fluoro-phenylethynyl)-3-hydroxy-cyclohexyl]-amide
3H-Imidazole-4-carboxylic acid [(±)-(1R,3R)-3-(3-fluoro-phenylethynyl)-3-hydroxy-cyclohexyl]-amide
N-[(1S,3S)-3-(3-Chloro-phenylethynyl)-3-hydroxy-cyclohexyl]-3,4-difluoro-benzamide
N-[(1R,3R)-3-(3-Chloro-phenylethynyl)-3-hydroxy-cyclohexyl]-3,4-difluoro-benzamide Pyridine-2-carboxylic acid [(1S,3S)-3-(3-chloro-phenylethynyl)-3-hydroxy-cyclohexyl]-amide Pyridine-2-carboxylic acid [(1R,3R)-3-(3-chloro-phenylethynyl)-3-hydroxy-cyclohexyl]-amide
N-[(1S,3S)-3-(3-Chloro-phenylethynyl)-3-hydroxy-cyclohexyl]-nicotinamide
N-[(1R,3R)-3-(3-Chloro-phenylethynyl)-3-hydroxy-cyclohexyl]-nicotinamide
Benzo[1,3]dioxole-2-carboxylic acid [(1S,3S)-3-(3-chloro-phenylethynyl)-3-hydroxy-cyclohexyl]-amide
5-Methyl-pyrazine-2-carboxylic acid [(1S,3S)-3-(3-chloro-phenylethynyl)-3-hydroxy-cyclohexyl]-amide
2-Methyl-furan-3-carboxylic acid [(1S,3S)-3-(3-chloro-phenylethynyl)-3-hydroxy-cyclohexyl]-amide
(R)-Tetrahydro-furan-2-carboxylic acid [(1R,3R)-3-(3-chloro-phenylethynyl)-3-hydroxy-cyclohexyl]-amide
(S)-Tetrahydro-furan-2-carboxylic acid [(1R,3R)-3-(3-chloro-phenylethynyl)-3-hydroxy-cyclohexyl]-amide
Isoxazole-5-carboxylic acid [(1S,3S)-3-(3-chloro-phenylethynyl)-3-hydroxy-cyclohexyl]-amide
5-Methyl-pyrazine-2-carboxylic acid [(1R,3R)-3-(3-chloro-phenylethynyl)-3-hydroxy-cyclohexyl]-amide
2-Methyl-furan-3-carboxylic acid [(1R,3R)-3-(3-chloro-phenylethynyl)-3-hydroxy-cyclohexyl]-amide
Isoxazole-5-carboxylic acid [(1R,3R)-3-(3-chloro-phenylethynyl)-3-hydroxy-cyclohexyl]-amide
5-Chloro-furan-2-carboxylic acid [(1R,3R)-3-(3-chloro-phenylethynyl)-3-hydroxy-cyclohexyl]-amide
5-Chloro-furan-2-carboxylic acid [(1S,3S)-3-(3-chloro-phenylethynyl)-3-hydroxy-cyclohexyl]-amide
(S)-Tetrahydro-furan-3-carboxylic acid [(1R,3R)-3-(3-chloro-phenylethynyl)-3-hydroxy-cyclohexyl]-amide
(R)-Tetrahydro-furan-3-carboxylic acid [(1R,3R)-3-(3-chloro-phenylethynyl)-3-hydroxy-cyclohexyl]-amide
N-[(1S,3S)-3-(3-Chloro-phenylethynyl)-3-hydroxy-cyclohexyl]-isonicotinamide
N-[(1R,3R)-3-(3-Chloro-phenylethynyl)-3-hydroxy-cyclohexyl]-isonicotinamide
3,5-Difluoro-pyridine-2-carboxylicacid [(1R,3R)-3-(3-chloro-phenylethynyl)-3-hydroxy-cyclohexyl]-amide
3,5-Difluoro-pyridine-2-carboxylicacid [(1S,3S)-3-(3-chloro-phenylethynyl)-3-hydroxy-cyclohexyl]-amide
6-Methyl-pyridine-2-carboxylic acid [(1S,3S)-3-(3-chloro-phenylethynyl)-3-hydroxy-cyclohexyl]-amide
6-Methyl-pyridine-2-carboxylic acid [(1R,3R)-3-(3-chloro-phenylethynyl)-3-hydroxy-cyclohexyl]-amide 5-Chloro-pyridine-2-carboxylic acid [(1R,3R)-3-(3-chloro-phenylethynyl)-3-hydroxy-cyclohexyl]-amide
5-Chloro-pyridine-2-carboxylic acid [(1S,3S)-3-(3-chloro-phenylethynyl)-3-hydroxy-cyclohexyl]-amide
6-Chloro-pyridine-2-carboxylic acid [(1R,3R)-3-(3-chloro-phenylethynyl)-3-hydroxy-cyclohexyl]-amide
6-Chloro-pyridine-2-carboxylic acid [(1S,3S)-3-(3-chloro-phenylethynyl)-3-hydroxy-cyclohexyl]-amide
5-Chloro-1-methyl-1H-pyrrole-2-carboxylic acid [(1R,3R)-3-(3-chloro-phenylethynyl)-3-hydroxy-cyclohexyl]-amide
5-Chloro-1-methyl-1H-pyrrole-2-carboxylic acid [(1S,3S)-3-(3-chloro-phenylethynyl)-3-hydroxy-cyclohexyl]-amide
5-Chloro-1H-pyrrole-2-carboxylic acid [(1R,3R)-3-(3-chloro-phenylethynyl)-3-hydroxy-cyclohexyl]-amide
5-Chloro-1H-pyrrole-2-carboxylic acid [(1S,3S)-3-(3-chloro-phenylethynyl)-3-hydroxy-cyclohexyl]-amide
N-[(1S,3S)-3-(3-Chloro-phenylethynyl)-3-hydroxy-cyclohexyl]-4-dimethylamino-benzamide
1H-Pyrrole-3-carboxylic acid [(1S,3S)-3-(3-chloro-phenylethynyl)-3-hydroxy-cyclohexyl]-amide
N-[(1S,3S)-3-(3-chloro-phenylethynyl)-3-hydroxy-cyclohexyl]-4-methyl-benzamide
N-[(1S,3S)-3-(3-Chloro-phenylethynyl)-3-hydroxy-cyclohexyl]-4-methyl-benzamide
N-[(1S,3S)-3-(3-Chloro-phenylethynyl)-3-hydroxy-cyclohexyl]-3-fluoro-benzamide
N-[(1S,3S)-3-(3-Chloro-phenylethynyl)-3-hydroxy-cyclohexyl]-2-ethyl-butyramide
N-[(1S,3S)-3-(3-Chloro-phenylethynyl)-3-hydroxy-cyclohexyl]-4-(2,5-dimethoxy-phenyl)-4-oxo-butyramide
2-(2-Benzyloxy-ethoxy)-N-[(1S,3S)-3-(3-chloro-phenylethynyl)-3-hydroxy-cyclohexyl]-acetamide
N-[(1S,3S)-3-(3-Chloro-phenylethynyl)-3-hydroxy-cyclohexyl]-2-phenyl-acetamide
N-[(1S,3S)-3-(3-Chloro-phenylethynyl)-3-hydroxy-cyclohexyl]-3-(1H-indol-4-yl)-propionamide
2-Benzo[1,3]dioxol-5-yl-N-[(1S,3S)-3-(3-chloro-phenylethynyl)-3-hydroxy-cyclohexyl]-acetamide
N-[(1S,3S)-3-(3-Chloro-phenylethynyl)-3-hydroxy-cyclohexyl]-2-phenoxy-propionamide
N-[(1S,3S)-3-(3-Chloro-phenylethynyl)-3-hydroxy-cyclohexyl]-2-(2-fluoro-phenyl)-acetamide
5-Hydroxy-1H-indole-2-carboxylic acid [(1S,3S)-3-(3-chloro-phenylethynyl)-3-hydroxy-cyclohexyl]-amide
1-Methyl-1H-pyrrole-2-carboxylic acid [(1S,3S)-3-(3-chloro-phenylethynyl)-3-hydroxy-cyclohexyl]-amide
N-[(1S,3S)-3-(3-Chloro-phenylethynyl)-3-hydroxy-cyclohexyl]-terephthalamic acid methyl ester
N-[(1S,3S)-3-(3-Chloro-phenylethynyl)-3-hydroxy-cyclohexyl]-2-(2-trifluoromethoxy-phenyl)-acetamide
5-Chloro-N-[(1S,3S)-3-(3-chloro-phenylethynyl)-3-hydroxy-cyclohexyl]-2-hydroxy-benzamide
N-[(1S,3S)-3-(3-Chloro-phenylethynyl)-3-hydroxy-cyclohexyl]-4-hydroxy-benzamide
N-[(1S,3S)-3-(3-Chloro-phenylethynyl)-3-hydroxy-cyclohexyl]-2-hydroxy-benzamide
4-Amino-N-[(1S,3S)-3-(3-chloro-phenylethynyl)-3-hydroxy-cyclohexyl]-benzamide
4-Amino-5-chloro-N-[(1S,3S)-3-(3-chloro-phenylethynyl)-3-hydroxy-
3-Amino-4-chloro-N-[(1S,3S)-3-(3-chloro-phenylethynyl)-3-hydroxy-cyclohexyl]-benzamide
3-Amino-N-[(1S,3S)-3-(3-chloro-phenylethynyl)-3-hydroxy-cyclohexyl]-4-methyl-benzamide
2-Amino-N-[(1S,3S)-3-(3-chloro-phenylethynyl)-3-hydroxy-cyclohexyl]-nicotinamide
N-[(1S,3S)-3-(3-Chloro-phenylethynyl)-3-hydroxy-cyclohexyl]-4-hydroxy-3-methoxy-benzamide
N-[(1S,3S)-3-(3-Chloro-phenylethynyl)-3-hydroxy-cyclohexyl]-2-fluoro-benzamide
N-[(1S,3S)-3-(3-Chloro-phenylethynyl)-3-hydroxy-cyclohexyl]-4-methanesulfonyl-benzamide
Pyridine-2-carboxylic acid [(1S,3S)-3-(3-chloro-phenylethynyl)-3-hydroxy-cyclohexyl]-amide
3-Amino-pyrazine-2-carboxylic acid [(1S,3S)-3-(3-chloro-phenylethynyl)-3-hydroxy-cyclohexyl]-amide
6-Amino-N-[(1S,3S)-3-(3-chloro-phenylethynyl)-3-hydroxy-cyclohexyl]-nicotinamide
4-(4-Amino-benzoylamino)-benzoic acid [(1R,3R)-3-(3-chloro-phenylethynyl)-3-hydroxy-cyclohexyl]-amide
2,6-Dioxo-1,2,3,6-tetrahydro-pyrimidine-4-carboxylic acid [(1S,3S)-3-(3-chloro-phenylethynyl)-3-hydroxy-cyclohexyl]-amide
N-[(1S,3S)-3-(3-Chloro-phenylethynyl)-3-hydroxy-cyclohexyl]-isonicotinamide
3-Chloro-N-[(1S,3S)-3-(3-chloro-phenylethynyl)-3-hydroxy-cyclohexyl]-benzamide
N-[(1S,3S)-3-(3-Chloro-phenylethynyl)-3-hydroxy-cyclohexyl]-2,3-dimethoxy-benzamide
N-[(1S,3S)-3-(3-Chloro-phenylethynyl)-3-hydroxy-cyclohexyl]-4-oxo-4-phenyl-butyramide
2-Chloro-N-[(1S,3S)-3-(3-chloro-phenylethynyl)-3-hydroxy-cyclohexyl]-nicotinamide
5-Bromo-N-[(1S,3S)-3-(3-chloro-phenylethynyl)-3-hydroxy-cyclohexyl]-nicotinamide
Isoquinoline-1-carboxylic acid [(1S,3S)-3-(3-chloro-phenylethynyl)-3-hydroxy-cyclohexyl]-amide
Pyrazine-2-carboxylic acid [(1S,3S)-3-(3-chloro-phenylethynyl)-3-hydroxy-cyclohexyl]-amide
3-Benzoyl-pyridine-2-carboxylic acid [(1S,3S)-3-(3-chloro-phenylethynyl)-3-hydroxy-cyclohexyl]-amide
N-[(1S,3S)-3-(3-Chloro-phenylethynyl)-3-hydroxy-cyclohexyl]-2-methyl-nicotinamide
Quinoxaline-2-carboxylic acid [(1S,3S)-3-(3-chloro-phenylethynyl)-3-hydroxy-cyclohexyl]-amide
Pyridazine-4-carboxylic acid [(1S,3S)-3-(3-chloro-phenylethynyl)-3-hydroxy-cyclohexyl]-amide
N-[(1S,3S)-3-(3-Chloro-phenylethynyl)-3-hydroxy-cyclohexyl]-2-methylsulfanyl-nicotinamide
N-[(1S,3S)-3-(3-Chloro-phenylethynyl)-3-hydroxy-cyclohexyl]-4-trifluoromethyl-nicotinamide
2-Chloro-N-[(1S,3S)-3-(3-chloro-phenylethynyl)-3-hydroxy-cyclohexyl]-isonicotinamide
2-Chloro-N-[(1S,3S)-3-(3-chloro-phenylethynyl)-3-hydroxy-cyclohexyl]-6-methyl-nicotinamide
6-Chloro-N-[(1S,3S)-3-(3-chloro-phenylethynyl)-3-hydroxy-cyclohexyl]-nicotinamide
2-Chloro-N-[(1S,3S)-3-(3-chloro-phenylethynyl)-3-hydroxy-cyclohexyl]-6-methyl-isonicotinamide
N-[(1S,3S)-3-(3-Chloro-phenylethynyl)-3-hydroxy-cyclohexyl]-2-(4,5-dimethoxy-3-oxo-1,3-dihydro-isobenzofuran-1-yl)-acetamide
1,4,5,6-Tetrahydro-cyclopentapyrazole-3-carboxylic acid [(1S,3S)-3-(3-chloro-phenylethynyl)-3-hydroxy-cyclohexyl]-amide
N-[(1S,3S)-3-(3-Chloro-phenylethynyl)-3-hydroxy-cyclohexyl]-3-(1H-indol-2-yl)-propionamide
6-[(1S,3S)-3-(3-Chloro-phenylethynyl)-3-hydroxy-cyclohexylcarbamoyl]-pyridine-2-carboxylic acid isopropyl ester Quinoline-6-carboxylic acid [(1S,3S)-3-(3-chloro-phenylethynyl)-3-hydroxy-cyclohexyl]-amide 5-Methyl-isoxazole-4-carboxylic acid [(1S,3S)-3-(3-chlorophenylethynyl)-3-hydroxy-cyclohexyl]-amide Benzofuran-3-carboxylic acid [(1S,3S)-3-(3-chloro-phenylethynyl)-3-hydroxy-cyclohexyl]-amide N-[(1S,3S)-3-(3-Chloro-phenylethynyl)-3-hydroxy-cyclohexyl]-2-(2-methoxy-phenoxy)-acetamide.

In a particular example o the present invention, there is provided a combination of the above listed exemplary compounds of formula (V) with at least one active agent selected from the group consisting of L-dopa, carbidopa, benserazide tolcapone or entacapone.

In a further embodiment, the mGluR modulator is a compound of the formula (VI)

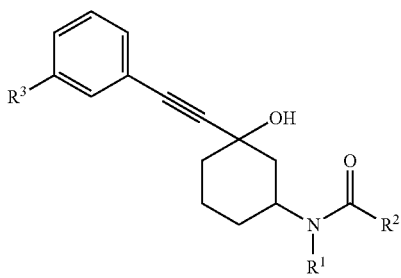
(VI)

wherein $R^1$ represents hydrogen or alkyl;

$R^2$ represents an unsubstituted or substituted heterocycle or $R^2$ represents an unsubstituted or substituted aryl;

$R^3$ represents alkyl or halogen;

in free base or acid addition salt form.

In another embodiment, the mGluR modulator is a compound of the formula (VII):

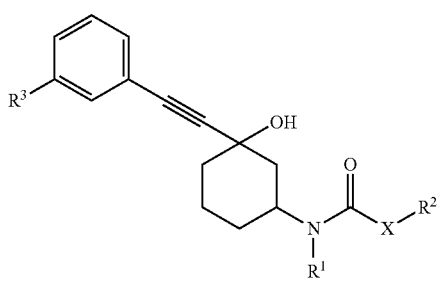
(VII)

wherein $R^1$ represents hydrogen or alkyl;

$R^2$ represents an unsubstituted or substituted heterocycle or $R^2$ represents an unsubstituted or substituted aryl;

$R^3$ represents alkyl or halogen;

X represents a single bond or an alkandiyl-group, optionally interrupted by one ore more oxygen atoms or carbonyl groups or carbonyloxy groups in free base or acid addition salt form.

In a further embodiment, the invention provides a compound of formula (VIII)

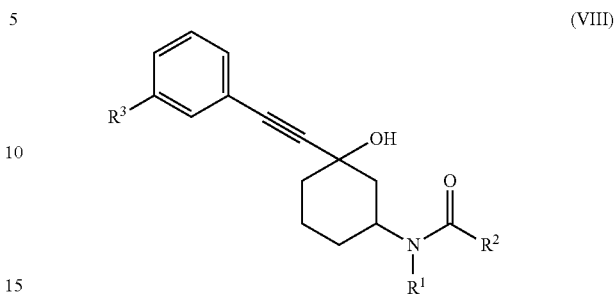
(VIII)

wherein $R^1$ represents hydrogen or alkyl;

$R^2$ represents an unsubstituted or substituted heterocycle or $R^2$ represents an unsubstituted or substituted aryl;

$R^3$ represents alkyl or halogen;

in free base or acid addition salt form.

Preferred substituents, preferred ranges of numerical values or preferred ranges of the radicals present in the formula (VII) and formula (VIII) are defined below.

$R^1$ preferably represents hydrogen or $C_{1-4}$ alkyl.

$R^1$ particularly preferably represents hydrogen.

$R^3$ preferably represents Fluoro, Chloro, $C_{1-4}$alkyl.

$R^3$ particularly preferably represents chloro or methyl.

$R^2$ preferably represents an unsubstituted or substituted heterocycle having 3-11 ring atoms and 1-4 hetero atoms; the hetero atoms being selected from the group consisting of N, O, S, the substituents being selected from the group consisting of Oxo (=O), Hydroxy, Halogen, Amino, Nitro, Cyano, $C_{1-4}$ Alkyl, $C_{1-4}$ Alkoxy, $C_{1-4}$ Alkoxyalkyl, $C_{1-4}$ Alkoxycarbonyl, $C_{1-4}$ Alkoxycarbonylalkyl, $C_{1-4}$ Halogenalkyl, $C_{6-10}$ Aryl, Halogen-$C_{6-10}$ Aryl, $C_{6-10}$ Aryloxy, $C_{6-10}$-Aryl-$C_{1-4}$ alkyl.

$R^2$ further preferably represents phenyl or substituted phenyl, the substituents being selected from the group consisting of Hydroxy, Amino, Halogen, Nitro, Cyano, $C_{1-4}$ Alkyl, $C_{1-4}$ Alkoxy, $C_{1-4}$ Alkoxyalkyl, $C_{1-4}$ Alkoxycarbonyl, $C_{1-4}$ Alkoxycarbonylalkyl, $C_{1-4}$ Halogenalkyl, $C_{8-10}$ Aryl, Halogen-$C_{6-10}$ Aryl, $C_{6-10}$ Aryloxy, $C_{6-10}$-Aryl-$C_{1-4}$ alkyl.

$R^2$ particularly preferably represents an unsubstituted, a single or twofold substituted heterocycle having 5-9 ring atoms and 1-3 hetero atoms; the hetero atoms being selected from the group consisting of N, O; the substituents being selected from the group consisting of Halogen, $C_{1-4}$ Alkyl.

$R^2$ particularly preferably represents an unsubstituted, a single or twofold substituted phenyl, the substituents being selected from the group consisting of fluoro, chloro, hydroxy, methyl, methoxy, methoxycarbonyl, trifluormethoxy, amino, dimethylamino, methylthio, methylsulfonyl.

$R^2$ very particularly preferably represents an unsubstituted, a single or twofold substituted heterocycle selected from the group consisting of

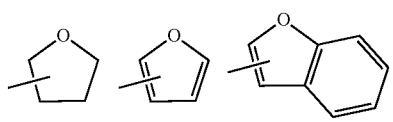

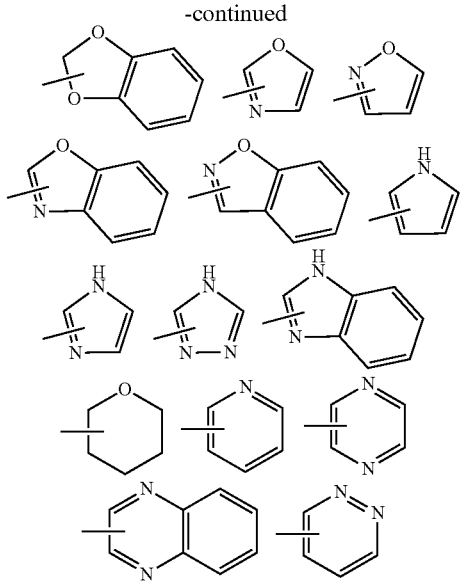

and the substituents selected from the group consisting of fluoro, chloro, methyl, methylthio, amino.

$R^2$ further very particularly preferably represents a substituent selected from the group consisting of

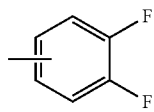

X preferably represents $C_{1-6}$ alkandiyl, $C_{1-6}$ alkandiyl with an oxygen group at the end or $C_{1-6}$ alkandiyl with an carbonyl group at the end, $C_{1-6}$alkandiyl with an carbonyloxy group at the end.

X particular preferably represents, methandiyl (—CH$_2$—), 1,2-ethanediyl (—CH$_2$—CH$_2$—), 1,1-ethanediyl ((—CH(CH$_3$)—), methandiyloxy (—O—CH$_2$—), 1,2-ethanediyloxy (—O—CH$_2$—CH$_2$—), 1,1-ethanediyloxy ((—O—CH(CH$_3$)—), methandiylcarbonyl (—CO—CH$_2$—), 1,2-ethanediylcarbonyl (—CO—CH$_2$—CH$_2$—), 1,1-ethanediylcarbonyl ((—CO—CH(CH$_3$)—), methandiylcarbonyloxy (—C(O)O—CH$_2$—), 1,2-ethanediylcarbonyloxy (—C(O)O—CH$_2$—CH$_2$—), 1,1-ethanediylcarbonyloxy ((—C(O)O—CH(CH$_3$)—). The functional groups as defined for X are preferably bound to the group $R^2$.

The abovementioned general or preferred radical definitions can be combined with one another at will, i.e. including combinations between the given preferred ranges. Further, individual definitions may not apply.

Preference according to the invention is given to compounds of the formula (VII) which contain a combination of the meanings mentioned above as being preferred.

Particular preference according to the invention is given to compounds of the formula (VII) which contain a combination of the meanings listed above as being particularly preferred.

Very particular preference according to the invention is given to the compounds of the formula (VII) which contain a combination of the meanings listed above as being very particularly preferred.

Preferred are compounds of formula (VII) wherein $R^2$ represents an unsubstituted or substituted heterocycle.

In a further embodiment, the invention provides a compound of formula (IX)

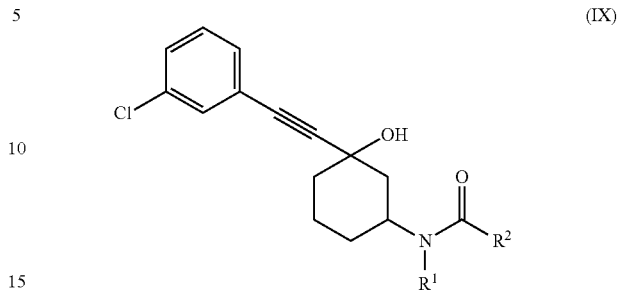

wherein $R^1$ and $R^2$ are as defined above.

In a further embodiment, the invention provides a compound of formula (IX) as defined above, wherein $R^2$ is as defined above and $R^1$ represents hydrogen.

Examples of compounds of formula (VII), (VIII) and (IX) include:

Furan-3-carboxylic acid [(1R,3R)-3-(3-chloro-phenylethynyl)-3-hydroxy-cyclohexyl]-amide
Furan-3-carboxylic acid [(1S,3S)-3-(3-chloro-phenylethynyl)-3-hydroxy-cyclohexyl]-amide
Furan-2-carboxylic acid [(1R,3R)-3-(3-chloro-phenylethynyl)-3-hydroxy-cyclohexyl]-amide
Furan-2-carboxylic acid [(1S,3S)-3-(3-chloro-phenylethynyl)-3-hydroxy-cyclohexyl]-amide
3H-Imidazole-4-carboxylic acid [(1R,3R)-3-(3-chloro-phenylethynyl)-3-hydroxy-cyclohexyl]-amide
3H-Imidazole-4-carboxylic acid [(1S,3S)-3-(3-chloro-phenylethynyl)-3-hydroxy-cyclohexyl]-amide
4H-[1,2,4]Triazole-3-carboxylic acid [(1R,3R)-3-(3-chloro-phenylethynyl)-3-hydroxy-cyclohexyl]-amide
4H-[1,2,4]Triazole-3-carboxylic acid [(1S,3S)-3-(3-chloro-phenylethynyl)-3-hydroxy-cyclohexyl]-amide
2-Methyl-furan-3-carboxylic acid [(±)-(1R,3R)-3-(3-chloro-phenylethynyl)-3-hydroxy-cyclohexyl]-amide
N-[(±)-(1R,3R)-3-(3-Chloro-phenylethynyl)-3-hydroxy-cyclohexyl]-3,4-difluoro-benzamide
Benzo[1,3]dioxole-2-carboxylic acid [(±)-(1R,3R)-3-(3-chloro-phenylethynyl)-3-hydroxy-cyclohexyl]-amide
5-Methyl-pyrazine-2-carboxylic acid [(±)-(1R,3R)-3-(3-chloro-phenylethynyl)-3-hydroxy-cyclohexyl]-amide
Quinoxaline-2-carboxylic acid [(±)-(1R,3R)-3-(3-chloro-phenylethynyl)-3-hydroxy-cyclohexyl]-amide
Benzofuran-2-carboxylic acid [(±)-(1R,3R)-3-(3-chloro-phenylethynyl)-3-hydroxy-cyclohexyl]-amide
Benzooxazole-2-carboxylic acid [(±)-(1R,3R)-3-(3-chloro-phenylethynyl)-3-hydroxy-cyclohexyl]-amide
2,5-Dimethyl-furan-3-carboxylic acid [(±)-(1R,3R)-3-(3-chloro-phenylethynyl)-3-hydroxy-cyclohexyl]-amide
(R,S)-Tetrahydro-furan-3-carboxylic acid [(±)-(1R,3R)-3-(3-chloro-phenylethynyl)-3-hydroxy-cyclohexyl]-amide
Furan-3-carboxylic acid ((1R,3R)-3-hydroxy-3-m-tolylethynyl-cyclohexyl)-amide
Furan-3-carboxylic acid ((1S,3S)-3-hydroxy-3-m-tolylethynyl-cyclohexyl)-amide
Furan-3-carboxylic acid ((±)-(1R,3R)-3-hydroxy-3-m-tolylethynyl-cyclohexyl)-amide
Furan-2-carboxylic acid ((1R,3R)-3-hydroxy-3-m-tolylethynyl-cyclohexyl)-amide
Furan-2-carboxylic acid ((1S,3S)-3-hydroxy-3-m-tolylethynyl-cyclohexyl)-amide Furan-2-carboxylic acid ((±)-(1R,3R)-3-hydroxy-3-m-tolyl-ethynyl-cyclohexyl)-amide
Isoxazole-5-carboxylic acid ((1R,3R)-3-hydroxy-3-m-tolyl-ethynyl-cyclohexyl)-amide
Isoxazole-5-carboxylic acid ((1S,3S)-3-hydroxy-3-m-tolyl-ethynyl-cyclohexyl)-amide
Isoxazole-5-carboxylic acid ((±)-(1R,3R)-3-hydroxy-3-m-tolylethynyl-cyclohexyl)-amide
5-Methyl-pyrazine-2-carboxylic acid ((±)-(1R,3R)-3-hydroxy-3-m-tolylethynyl-cyclohexyl)-amide
4H-[1,2,4]Triazole-3-carboxylic acid ((±)-(1R,3R)-3-hydroxy-3-m-tolylethynyl-cyclohexyl)-amide
3H-Imidazole-4-carboxylic acid ((±)-(1R,3R)-3-hydroxy-3-m-tolylethynyl-cyclohexyl)-amide
Tetrahydro-pyran-4-carboxylic acid ((±)-(1R,3R)-3-hydroxy-3-m-tolylethynyl-cyclohexyl)-amide
1-Methyl-1H-imidazole-4-carboxylic acid ((±)-(1R,3R)-3-hydroxy-3-m-tolylethynyl-cyclohexyl)-amide
(R,S)-Tetrahydro-furan-2-carboxylic acid ((±)-(1R,3R)-3-hydroxy-3-m-tolylethynyl-cyclohexyl)-amide
(R,S)-Tetrahydro-furan-3-carboxylic acid ((±)-(1R,3R)-3-hydroxy-3-m-tolylethynyl-cyclohexyl)-amide
Furan-3-carboxylic acid [(1R,3R)-3-(3-fluoro-phenylethynyl)-3-hydroxy-cyclohexyl]-amide
Furan-3-carboxylic acid [(1S,3S)-3-(3-fluoro-phenylethynyl)-3-hydroxy-cyclohexyl]-amide
Furan-2-carboxylic acid [(1R,3R)-3-(3-fluoro-phenylethynyl)-3-hydroxy-cyclohexyl]-amide
Furan-2-carboxylic acid [(1S,3S)-3-(3-fluoro-phenylethynyl)-3-hydroxy-cyclohexyl]-amide
3H-Imidazole-4-carboxylic acid [(±)-(1R,3R)-3-(3-fluoro-phenylethynyl)-3-hydroxy-cyclohexyl]-amide
N-[(1S,3S)-3-(3-Chloro-phenylethynyl)-3-hydroxy-cyclohexyl]-3,4-difluoro-benzamide
N-[(1R,3R)-3-(3-Chloro-phenylethynyl)-3-hydroxy-cyclohexyl]-3,4-difluoro-benzamide
Pyridine-2-carboxylic acid [(1S,3S)-3-(3-chloro-phenylethynyl)-3-hydroxy-cyclohexyl]-amide
Pyridine-2-carboxylic acid [(1R,3R)-3-(3-chloro-phenylethynyl)-3-hydroxy-cyclohexyl]-amide
N-[(1S,3S)-3-(3-Chloro-phenylethynyl)-3-hydroxy-cyclohexyl]-nicotinamide
N-[(1R,3R)-3-(3-Chloro-phenylethynyl)-3-hydroxy-cyclohexyl]-nicotinamide
Benzo[1,3]dioxole-2-carboxylic acid [(1S,3S)-3-(3-chloro-phenylethynyl)-3-hydroxy-cyclohexyl]-amide
5-Methyl-pyrazine-2-carboxylic acid [(1S,3S)-3-(3-chloro-phenylethynyl)-3-hydroxy-cyclohexyl]-amide
2-Methyl-furan-3-carboxylic acid [(1S,3S)-3-(3-chloro-phenylethynyl)-3-hydroxy-cyclohexyl]-amide
(R)-Tetrahydro-furan-2-carboxylic acid [(1R,3R)-3-(3-chloro-phenylethynyl)-3-hydroxy-cyclohexyl]-amide
(S)-Tetrahydro-furan-2-carboxylic acid [(1R,3R)-3-(3-chloro-phenylethynyl)-3-hydroxy-cyclohexyl]-amide
Isoxazole-5-carboxylic acid [(1S,3S)-3-(3-chloro-phenylethynyl)-3-hydroxy-cyclohexyl]-amide
5-Methyl-pyrazine-2-carboxylic acid [(1R,3R)-3-(3-chloro-phenylethynyl)-3-hydroxy-cyclohexyl]-amide
2-Methyl-furan-3-carboxylic acid [(1R,3R)-3-(3-chloro-phenylethynyl)-3-hydroxy-cyclohexyl]-amide
Isoxazole-5-carboxylic acid [(1R,3R)-3-(3-chloro-phenylethynyl)-3-hydroxy-cyclohexyl]-amide
5-Chloro-furan-2-carboxylic acid [(1R,3R)-3-(3-chloro-phenylethynyl)-3-hydroxy-cyclohexyl]-amide
5-Chloro-furan-2-carboxylic acid [(1S,3S)-3-(3-chloro-phenylethynyl)-3-hydroxy-cyclohexyl]-amide
(S)-Tetrahydro-furan-3-carboxylic acid [(1R,3R)-3-(3-chloro-phenylethynyl)-3-hydroxy-cyclohexyl]-amide
(R)-Tetrahydro-furan-3-carboxylic acid [(1R,3R)-3-(3-chloro-phenylethynyl)-3-hydroxy-cyclohexyl]-amide
N-[(1S,3S)-3-(3-Chloro-phenylethynyl)-3-hydroxy-cyclohexyl]-isonicotinamide
N-[(1R,3R)-3-(3-Chloro-phenylethynyl)-3-hydroxy-cyclohexyl]-isonicotinamide
3,5-Difluoro-pyridine-2-carboxylic acid [(1R,3R)-3-(3-chloro-phenylethynyl)-3-hydroxy-cyclohexyl]-amide
3,5-Difluoro-pyridine-2-carboxylic acid [(1S,3S)-3-(3-chloro-phenylethynyl)-3-hydroxy-cyclohexyl]-amide
6-Methyl-pyridine-2-carboxylic acid [(1S,3S)-3-(3-chloro-phenylethynyl)-3-hydroxy-cyclohexyl]-amide
6-Methyl-pyridine-2-carboxylic acid [(1R,3R)-3-(3-chloro-phenylethynyl)-3-hydroxy-cyclohexyl]-amide
5-Chloro-pyridine-2-carboxylic acid [(1R,3R)-3-(3-chloro-phenylethynyl)-3-hydroxy-cyclohexyl]-amide
5-Chloro-pyridine-2-carboxylic acid [(1S,3S)-3-(3-chloro-phenylethynyl)-3-hydroxy-cyclohexyl]-amide
6-Chloro-pyridine-2-carboxylic acid [(1R,3R)-3-(3-chloro-phenylethynyl)-3-hydroxy-cyclohexyl]-amide
6-Chloro-pyridine-2-carboxylic acid [(1S,3S)-3-(3-chloro-phenylethynyl)-3-hydroxy-cyclohexyl]-amide
5-Chloro-1-methyl-1H-pyrrole-2-carboxylic acid [(1R,3R)-3-(3-chloro-phenylethynyl)-3-hydroxy-cyclohexyl]-amide
5-Chloro-1-methyl-1H-pyrrole-2-carboxylic acid [(1S,3S)-3-(3-chloro-phenylethynyl)-3-hydroxy-cyclohexyl]-amide
5-Chloro-1H-pyrrole-2-carboxylic acid [(1R,3R)-3-(3-chloro-phenylethynyl)-3-hydroxy-cyclohexyl]-amide
5-Chloro-1H-pyrrole-2-carboxylic acid [(1S,3S)-3-(3-chloro-phenylethynyl)-3-hydroxy-cyclohexyl]-amide
N-[(1S,3S)-3-(3-Chloro-phenylethynyl)-3-hydroxy-cyclohexyl]-4-dimethylamino-benzamide
1H-Pyrrole-3-carboxylic acid [(1S,3S)-3-(3-chloro-phenylethynyl)-3-hydroxy-cyclohexyl]-amide
N-[(1S,3S)-3-(3-chloro-phenylethynyl)-3-hydroxy-cyclohexyl]-4-methyl-benzamide
N-[(1S,3S)-3-(3-Chloro-phenylethynyl)-3-hydroxy-cyclohexyl]-4-methyl-benzamide
N-[(1S,3S)-3-(3-Chloro-phenylethynyl)-3-hydroxy-cyclohexyl]-3-fluoro-benzamide
N-[(1S,3S)-3-(3-Chloro-phenylethynyl)-3-hydroxy-cyclohexyl]-2-ethyl-butyramide
N-[(1S,3S)-3-(3-Chloro-phenylethynyl)-3-hydroxy-cyclohexyl]-4-(2,5-dimethoxy-phenyl)-4-oxo-butyramide
2-(2-Benzyloxy-ethoxy)-N-[(1S,3S)-3-(3-chloro-phenylethynyl)-3-hydroxy-cyclohexyl]-acetamide
N-[(1S,3S)-3-(3-Chloro-phenylethynyl)-3-hydroxy-cyclohexyl]-2-phenyl-acetamide
N-[(1S,3S)-3-(3-Chloro-phenylethynyl)-3-hydroxy-cyclohexyl]-3-(1H-indol-4-yl)-propionamide
2-Benzo[1,3]dioxol-5-yl-N-[(1S,3S)-3-(3-chloro-phenylethynyl)-3-hydroxy-cyclohexyl]-acetamide
N-[(1S,3S)-3-(3-Chloro-phenylethynyl)-3-hydroxy-cyclohexyl]-2-phenoxy-propionamide
N-[(1S,3S)-3-(3-Chloro-phenylethynyl)-3-hydroxy-cyclohexyl]-2-(2-fluoro-phenyl)-acetamide
5-Hydroxy-1H-indole-2-carboxylic acid [(1S,3S)-3-(3-chloro-phenylethynyl)-3-hydroxy-cyclohexyl]-amide
1-Methyl-1H-pyrrole-2-carboxylic acid [(1S,3S)-3-(3-chloro-phenylethynyl)-3-hydroxy-cyclohexyl]-amide
N-[(1S,3S)-3-(3-Chloro-phenylethynyl)-3-hydroxy-cyclohexyl]-terephthalamic acid methyl ester N-[(1S,3S)-3-(3-Chloro-phenylethynyl)-3-hydroxy-cyclohexyl]-2-(2-trifluoromethoxy-phenyl)-acetamide
5-Chloro-N-[(1S,3S)-3-(3-chloro-phenylethynyl)-3-hydroxy-cyclohexyl]-2-hydroxy-benzamide
N-[(1S,3S)-3-(3-Chloro-phenylethynyl)-3-hydroxy-cyclohexyl]-4-hydroxy-benzamide
N-[(1S,3S)-3-(3-Chloro-phenylethynyl)-3-hydroxy-cyclohexyl]-2-hydroxy-benzamide
4-Amino-N-[(1S,3S)-3-(3-chloro-phenylethynyl)-3-hydroxy-cyclohexyl]-benzamide
4-Amino-5-chloro-N-[(1S,3S)-3-(3-chloro-phenylethynyl)-3-hydroxy-cyclohexyl]-2-methoxy-benzamide
3-Amino-4-chloro-N-[(1S,3S)-3-(3-chloro-phenylethynyl)-3-hydroxy-cyclohexyl]-benzamide
3-Amino-N-[(1S,3S)-3-(3-chloro-phenylethynyl)-3-hydroxy-cyclohexyl]-4-methyl-benzamide
2-Amino-N-[(1S,3S)-3-(3-chloro-phenylethynyl)-3-hydroxy-cyclohexyl]-nicotinamide
N-[(1S,3S)-3-(3-Chloro-phenylethynyl)-3-hydroxy-cyclohexyl]-4-hydroxy-3-methoxy-benzamide
N-[(1S,3S)-3-(3-Chloro-phenylethynyl)-3-hydroxy-cyclohexyl]-2-fluoro-benzamide
N-[(1S,3S)-3-(3-Chloro-phenylethynyl)-3-hydroxy-cyclohexyl]-4-methanesulfonyl-benzamide
Pyridine-2-carboxylic acid [(1S,3S)-3-(3-chloro-phenylethynyl)-3-hydroxy-cyclohexyl]-amide
3-Amino-pyrazine-2-carboxylic acid [(1S,3S)-3-(3-chloro-phenylethynyl)-3-hydroxy-cyclohexyl]-amide
6-Amino-N-[(1S,3S)-3-(3-chloro-phenylethynyl)-3-hydroxy-cyclohexyl]-nicotinamide
4-(4-Amino-benzoylamino)-benzoic acid [(1R,3R)-3-(3-chloro-phenylethynyl)-3-hydroxy-cyclohexyl]-amide
2,6-Dioxo-1,2,3,6-tetrahydro-pyrimidine-4-carboxylic acid [(1S,3S)-3-(3-chloro-phenylethynyl)-3-hydroxy-cyclohexyl]-amide
N-[(1S,3S)-3-(3-Chloro-phenylethynyl)-3-hydroxy-cyclohexyl]-isonicotinamide
3-Chloro-N-[(1S,3S)-3-(3-chloro-phenylethynyl)-3-hydroxy-cyclohexyl]-benzamide
N-[(1S,3S)-3-(3-Chloro-phenylethynyl)-3-hydroxy-cyclohexyl]-2,3-dimethoxy-benzamide
N-[(1S,3S)-3-(3-Chloro-phenylethynyl)-3-hydroxy-cyclohexyl]-4-oxo-4-phenyl-butyramide
2-Chloro-N-[(1S,3S)-3-(3-chloro-phenylethynyl)-3-hydroxy-cyclohexyl]-nicotinamide
5-Bromo-N-[(1S,3S)-3-(3-chloro-phenylethynyl)-3-hydroxy-cyclohexyl]-nicotinamide
Isoquinoline-1-carboxylic acid [(1S,3S)-3-(3-chloro-phenylethynyl)-3-hydroxy-cyclohexyl]-amide
Pyrazine-2-carboxylic acid [(1S,3S)-3-(3-chloro-phenylethynyl)-3-hydroxy-cyclohexyl]-amide
3-Benzoyl-pyridine-2-carboxylic acid [(1S,3S)-3-(3-chloro-phenylethynyl)-3-hydroxy-cyclohexyl]-amide
N-[(1S,3S)-3-(3-Chloro-phenylethynyl)-3-hydroxy-cyclohexyl]-2-methyl-nicotinamide
Quinoxaline-2-carboxylic acid [(1S,3S)-3-(3-chloro-phenylethynyl)-3-hydroxy-cyclohexyl]-amide
Pyridazine-4-carboxylic acid [(1S,3S)-3-(3-chloro-phenylethynyl)-3-hydroxy-cyclohexyl]-amide
N-[(1S,3S)-3-(3-Chloro-phenylethynyl)-3-hydroxy-cyclohexyl]-2-methylsulfanyl-nicotinamide
N-[(1S,3S)-3-(3-Chloro-phenylethynyl)-3-hydroxy-cyclohexyl]-4-trifluoromethyl-nicotinamide
2-Chloro-N-[(1S,3S)-3-(3-chloro-phenylethynyl)-3-hydroxy-cyclohexyl]-isonicotinamide
2-Chloro-N-[(1S,3S)-3-(3-chloro-phenylethynyl)-3-hydroxy-cyclohexyl]-6-methyl-nicotinamide
6-Chloro-N-[(1S,3S)-3-(3-chloro-phenylethynyl)-3-hydroxy-cyclohexyl]-nicotinamide
2-Chloro-N-[(1S,3S)-3-(3-chloro-phenylethynyl)-3-hydroxy-cyclohexyl]-6-methyl-isonicotinamide
N-[(1S,3S)-3-(3-Chloro-phenylethynyl)-3-hydroxy-cyclohexyl]-2-(4,5-dimethoxy-3-oxo-1,3-dihydro-isobenzofuran-1-yl)-acetamide
1,4,5,6-Tetrahydro-cyclopentapyrazole-3-carboxylic acid [(1S,3S)-3-(3-chloro-phenylethynyl)-3-hydroxy-cyclohexyl]-amide
N-[(1S,3S)-3-(3-Chloro-phenylethynyl)-3-hydroxy-cyclohexyl]-3-(1H-indol-2-yl)-propionamide
6-[(1S,3S)-3-(3-Chloro-phenylethynyl)-3-hydroxy-cyclohexylcarbamoyl]-pyridine-2-carboxylic acid isopropyl ester
Quinoline-6-carboxylic acid [(1S,3S)-3-(3-chloro-phenylethynyl)-3-hydroxy-cyclohexyl]-amide
5-Methyl-isoxazole-4-carboxylic acid [(1S,3S)-3-(3-chloro-phenylethynyl)-3-hydroxy-cyclohexyl]-amide
Benzofuran-3-carboxylic acid [(1S,3S)-3-(3-chloro-phenylethynyl)-3-hydroxy-cyclohexyl]-amide
N-[(1S,3S)-3-(3-Chloro-phenylethynyl)-3-hydroxy-cyclohexyl]-2-(2-methoxy-phenoxy)-acetamide In a particular example of the present invention, there is provided a combination of the above listed exemplary compounds of formulae (VII), (VIII) and (IX) with at least one active agent selected from the group consisting of L-dopa, carbidopa, benserazide tolcapone or entacapone.

In another example, there is provided a combination of an Octahydroindole in combination with entacapone.

In a further example, there is provided a combination of an Octahydroindole in combination with L-dopa, carbidpoa and entacapone, and example of which is a combination of an Octahydroindole with Stalevo®.

In further examples, the mGluR modulator is an mGluR5 modulator and is an Octahydroindole, e.g. 4-Hydroxy-4-m-tolylethynyl-octahydro-indole-1-carboxylic acid methyl ester.

The present invention therefore includes the combination of 4-Hydroxy-4-m-tolylethynyl-octahydro-indole-1-carboxylic acid methyl ester and one or more of L-dopa, carbidopa, benserazide tolcapone, entacapone, bromocriptine, pergolide, pramipexole, ropinirole, cabergoline, apomorphine or lisuride.

Further examples of mGluR, in particular mGluR5, modulators include compounds of the formula (I) as defined in WO 2004/014881 and compounds of the formula (I) as defined in WO 2007/021575; the contents of these publications are incorporated herein by reference.

The mGluR modulators as described herein may exhibit a marked and selective modulating, especially antagonistic, action at human mGluRs, in particular mGluR5s. This can be determined in vitro for example at recombinant human metabotropic glutamate receptors, especially PLC-coupled subtypes thereof such as mGluR5, using different procedures like, for example, measurement of the inhibition of the agonist induced elevation of intracellular $Ca^{2+}$ concentration in accordance with L. P. Daggett et al., Neuropharm. Vol. 34, pages 871-886 (1995), P. J. Flor et al., J. Neurochem. Vol. 67, pages 58-63 (1996) or by determination to what extent the agonist induced elevation of the inositol phosphate turnover is inhibited as described by T. Knoepfel et al., Eur. J. Pharmacol. Vol. 288, pages 389-392 (1994), L. P. Daggett et al., Neuropharm. Vol. 67, pages 58-63 (1996) and references cited therein. Isolation and expression of human mGluR subtypes are described in U.S. Pat. No. 5,521,297. Selected agents of the invention show IC50 values for the inhibition of the agonist (e.g. glutamate or quisqualate) induced elevation of intracellular Ca2+ concentration or the agonist (e.g. glutamate or quisqualate) induced inositol phosphate turnover, measured in recombinant cells expressing hmGluR5a of about 1 nM to about 50 µM.

The mGluR modulators as described herein, in combination as described herein or alone are useful in the treatment, prevention or delay of progression of Parkinson's Disease and disorders associated with Parkinson's Disease. Parkinson's Disease is a degenerative disorder of the central nervous system that often impairs the sufferer's motor skills and speech. Characteristics of Parkinson's Disease are varied and include one or more of the following: tremor, rigidity, bradykinesia, akinesia, gait and postural disturbances, postural instability, speech and swallowing disturbances and cognitive impairment e.g. memory loss, dementia and slowed reaction times. The mGluR modulators as described herein, in combination as described herein or alone may be useful to treat, prevent or delay the progression of one or more of the characteristics of Parkinson's Disease.

In one embodiment, the mGluR modulators as described herein, in combination as described herein or alone are useful in the treatment, prevention or delay of progression of disorders which are associated with Parkinson's Disease. An example of such a disorder is Parkinson's dyskinesia e.g. Parkinson's Disease L-dopa induced dyskinesia. Parkinson's dyskinesia often, although not exclusively, occurs as a side-effect of treatment of Parkinson's disease with levodopa (L-dopa), a precursor of dopamine. Characteristics of Parkinson's dyskinesia include motor impairment, e.g. the appearance of slow and uncoordinated involuntary movements, shaking, stiffness and problems walking. Patients treated with L-dopa often have reduced symptoms of Parkinson's disease but they experience increasing difficulties to remain standing or even sifting. After prolonged use of L-dopa, a majority of patients develop dyskinesia.

Dyskinesia can occur at any time during the cycle of treatment with L-dopa. In one embodiment, the mGluR modulators as described herein, in combination as described herein or alone are for the treatment of dyskinesia which occurs at the time of peak L-dopa plasma concentrations in the patient. In one embodiment, the mGluR modulators as described herein, in combination as described herein or alone are for the treatment of dyskinesia which occurs when the L-dopa plasma concentrations in a patient rise or fall (diphasic dyskinesia).

Dyskinesia can also develop in Parkinson's disease sufferers who do not take L-dopa. In one embodiment, the compounds are for the treatment of non-L-dope induced Parkinson's dyskinesia.

Treatment may comprise a reduction in the characteristics associated with Parkinson's dyskinesia, including for example, although not limited to, a reduction in the scale of involuntary movements, a reduction in the number of involuntary movements, an improvement in the ability to carry out normal tasks, an improved ability to walk, increased period of time between episodes of dyskinesia.

In the case of prophylactic treatment, the mGluR modulators as described herein, in combination as described herein or alone may be used to delay or prevent the onset of Parkinson's dyskinesia.

For the above-mentioned indications (the conditions and disorders) the appropriate dosage will vary depending upon, for example, the compound employed, the host, the mode of administration and the nature and severity of the condition being treated. However, in general, satisfactory results in animals are indicated to be obtained at a daily dosage of from about 0.01 to about 100 mg/kg body weight, preferably from about 0.1 to about 10 mg/kg body weight, e.g. 1 mg/kg. In larger mammals, for example humans, an indicated daily dosage is in the range from about 0.1 to about 1000 mg, preferably from about 1 to about 400 mg, most preferably from about 10 to about 100 mg of an mGluR, e.g. mGluR5, antagonist or other modulator conveniently administered, for example, in divided doses up to four times a day.

For use according to the invention, an mGluR modulator (e.g. an mGluR5 modulator, in particular an mGluR5 antagonist) may be administered as single active agent or in combination with other active agents, in any usual manner, e.g. orally, for example in the form of tablets or capsules, or parenterally, for example in the form of injection solutions or suspensions.

Moreover, the present invention provides a pharmaceutical composition comprising an mGluR modulator (e.g. an mGluR5 modulator, in particular an mGluR5 antagonist) in association with at least one pharmaceutical carrier or diluent for use in the treatment of Parkinson's Disease. In one embodiment, the composition is for use in the treatment of Parkinson's dyskinesia e.g. Parkinson's Disease L-dopa induced dyskinesia. Such compositions may be manufactured in conventional manner. Unit dosage forms may contain, for example, from about 2.5 to about 25 mg of one or more mGluR modulator, e.g. mGluR5 antagonist or other modulator.

The pharmaceutical compositions according to the invention are compositions for enteral, such as nasal, rectal or oral, or parenteral, such as intramuscular or intravenous, administration to warm-blooded animals (human beings and animals) that comprise an effective dose of the pharmacological active ingredient alone or together with a significant amount of a pharmaceutically acceptable carrier. The dose of the active ingredient depends on the species of warm-blooded animal, body weight, age and individual condition, individual pharmacokinetic data, the disease to be treated and the mode of administration.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragees, tablets or capsules.

The phamasic compositions of the present invention are prepared in a manner known per se, for example by means of conventional dissolving, lyophilizing, mixing, granulating or confectioning processes. Such processes are exemplified in WO 2005/079802, WO 2003/047581, WO 2004/000316, WO 2005/044265, WO 2005/044266, WO 2005/044267, WO 2006/114262 and WO 2007/071358.

Pharmaceutical compositions and medicaments may be described as mixtures of two or more components "by volume," which is herein defined as the volume due to one component divided by the volume of all components of the composition. This ratio may be converted to or reported as a percentage of the total composition volume. Such a quantity may also be indicated by "v/v" or "percent v/v." Similarly, the phrases "by weight" and "by mass" describe the weight or mass due to one component divided by the weight or mass of all components of the composition. This ratio may be converted to or reported as a percentage of the total composition weight or mass. Such a quantity may also be indicated by "w/w", "mass percent," or percent w/w."

A further aspect of the present invention is a kit for the prevention of, delay of progression of, treatment of a disease or condition according to the present invention comprising (a) an amount of an mGluR modulator or a pharmaceutically acceptable salt thereof in a first unit dosage form;
(b) an amount of at least one active ingredient selected from L-dopa, or a dopa decarboxylase inhibitor, or a catechol-O-methyl transferase inhibitor, or a dopamine agonist or, in each case, where appropriate, a pharmaceutically acceptable salt thereof; and
(c) a container for containing said first, second etc. unit forms.

In a variation thereof, the present invention likewise relates to a "kit-of-parts", for example, in the sense that the components to be combined according to the present invention can be dosed independently or by use of different fixed combinations with distinguished amounts of the components, i.e. simultaneously or at different time points.

The parts of the kit of parts can then e.g. be administered simultaneously or chronologically staggered, that is at different time points and with equal or different time intervals for any part of the kit of parts. Preferably, the time intervals are chosen such that the effect on the treated disease or condition in the combined use of the parts is larger than the effect that would be obtained by use of only any one of the components.

The present invention thus also relates to a kit of parts comprising
(a) an amount of an mGluR modulator or a pharmaceutically acceptable salt thereof in a first unit dosage form;
(b) an amount of at least one active ingredient selected from L-dopa, or a dopa decarboxylase inhibitor, or a catechol-O-methyl transferase inhibitor, or a dopamine agonist or, in each case, where appropriate, a pharmaceutically acceptable salt thereof, in the form of two or three or more separate units of the components (a) to (b), especially for the prevention of, delay of progression of, treatment of a disease or condition according to the present invention.

The invention furthermore relates to a commercial package comprising the combination according to the present invention together with instructions for simultaneous, separate or sequential use.

In a preferred embodiment, the (commercial) product is a commercial package comprising as active ingredients the combination according to the present invention (in the form of two or three or more separate units of the components (a) or (b)), together with instructions for its simultaneous, separate or sequential use, or any combination thereof, in the delay of progression or treatment of the diseases as mentioned herein.

All the preferences mentioned herein apply to the combination, composition, use, method of treatment, "kit of parts" and commercial package of the invention.

These pharmaceutical preparations are for enteral, such as oral, and also rectal or parenteral, administration to homeotherms, with the preparations comprising the pharmacological active compound either alone or together with customary pharmaceutical auxiliary substances. For example, the pharmaceutical preparations consist of from about 0.1% to 90%, preferably of from about 1% to about 80%, of the active compound. Pharmaceutical preparations for enteral or parenteral, and also for ocular, administration are, for example, in unit dose forms, such as coated tablets, tablets, capsules or suppositories and also ampoules. These are prepared in a manner that is known per se, for example using conventional mixing, granulation, coating, solubilizing or lyophilizing processes. Thus, pharmaceutical preparations for oral use can be obtained by combining the active compound(s) with solid excipients, if desired granulating a mixture which has been obtained, and, if required or necessary, processing the mixture or granulate into tablets or coated tablet cores after having added suitable auxiliary substances.

The dosage of the active compound can depend on a variety of factors, such as mode of administration, homeothermic species, age and/or individual condition.

Preferred dosages for the active ingredients of the pharmaceutical combination according to the present invention are therapeutically effective dosages, especially those which are commercially available.

Normally, in the case of oral administration, an approximate daily dose of from about 1 mg to about 360 mg is to be estimated e.g. for a patient of approximately 75 kg in weight.

The dosage of the active compound can depend on a variety of factors, such as mode of administration, homeothermic species, age and/or individual condition.

The pharmaceutical composition according to the present invention as described hereinbefore may be used for simultaneous use or sequential use in any order, for separate use or as a fixed combination.

The action of mGluR modulators, e.g. mGluR antagonists on Parkinson's Disease and associated disorders e.g. Parkinson's dyskensia, for example, Parkinson's Disease levodopa (L-dopa) induced Parkinson's dyskensia as described herein, may be conducted in the following way.

Firstly, it has been found through imaging techniques that the compounds of the present invention are able to penetrate the brain and bind to mGluR receptors, in particular mGluR5 receptors. Secondly, it has been observed that patients taking a compound, such as an mGluR modulators as described herein have shown an increase in cognition or the like.

Clinical testing of the compounds as mentioned herein may be conducted, for example, in one of the following study designs. The skilled physician may look at a number of aspects of a patients behaviours and abilities. The skilled person will of course realise that such studies are considered as guidelines and the certain aspects of the studies may be modified and redefined depending on the circumstance and environment, for example.

The usefulness of the mGluR modulators as described herein, in combination as described or alone, in the treatment of the above-mentioned disorders can be confirmed in a range of standard tests including those indicated below:

Clinical Design: Improvement Trials
Trial A: Normal Patient Population
A patient population, with a normal control is dosed once a day for a week or longer tested. The test is designed to allow for improvement, I.e. that there is a measurable parameter increase of the impaired function The patients are tested at the beginning and at the end of the dosage period and the results are compared and analysed.
Trial B: Deficit population
A patient population with a deficit associated with Parkinson's Disease and associated disorders e.g. Parkinson's dyskensia, for example, Parkinson's Disease levodopa (L-dopa) induced Parkinson's dyskensia is dosed once a day for a week or longer and tested. The test is designed to allow for improvement, I.e. that there is a measurable parameter increase of the impaired function. The patients are tested at the beginning and at the end of the dosage period and the results are compared and analysed.
Considerations for Designing a Trial
When designing a trial, the skilled person will appreciate the need to protect both against floor and ceiling effects. In other words, the study designing should allow cognition to the measurably raised or lowered.
Conditions that artificially impair a function, e.g. cognition, are one way to test enhancement of that function. Such conditions are, for example, sleep deprivation and pharmacological challenges.
Placebo control is required for all trials.
In assessing the data, evaluation of the likelihood of learning and practice effects from repeat assessments must be made. The likelihood of such effects contaminating the data to produce false positives should be taken in to account when designing the test, e.g. the tests should not be identical (e.g. commit the same list of words to memory) but designed to study the same mechanism. Other countermeasures may include single testing at the end of a trial only.

The invention claimed is:

1. A pharmaceutical composition comprising a therapeutically effective amount of the mGluR5 antagonist (−)-(3aR,4S,7aR)-4-Hydroxy-4-m-tolyethynyl-octahydro-indole-1-carboxylic acid methyl ester, or a pharmaceutically acceptable salt thereof, and
   i) L-dopa,
   or a pharmaceutically acceptable salt thereof.

2. A kit comprising:
   a) a therapeutically effective amount of the mGluR5 antagonist (−)-(3aR,4S,7aR)-4-Hydroxy-4-m-tolyethynyl-octahydro-indole-1-carboxylic acid methyl ester, or a pharmaceutically acceptable salt thereof, in a first unit dosage form;
   b) an amount of at least one active ingredient selected from L-dopa or a pharmaceutically acceptable salt thereof, in (an) additional unit dosage form(s); and
   c) a container for containing said first unit dosage form and said additional unit dosage form(s); and
   d) instructions for using the first and additional unit dosage forms in the treatment, delay in onset or delay of progression of Parkinson's disease and/or a disorder associated with Parkinson's disease.

* * * * *